US012036314B2

(12) United States Patent
Myung et al.

(10) Patent No.: US 12,036,314 B2
(45) Date of Patent: Jul. 16, 2024

(54) COMPOSITIONS AND METHODS FOR IN SITU-FORMING TISSUE CONSTRUCTS

(71) Applicants: The Board of Trustees of the Leland Stanford Junior University, Stanford, CA (US); The U.S. Government Represented by the Department of Veterans Affairs, NW Washington, DC (US)

(72) Inventors: David Myung, Stanford, CA (US); Sarah Hull, Stanford, CA (US); Sarah Heilshorn, Mountain View, CA (US); Christopher Lindsay, San Mateo, CA (US); Christopher Madl, Los Altos, CA (US); Hyun Jong Lee, Gyeonggi-do (KR)

(73) Assignees: The Board of Trustees of the Leland Stanford Junior University, Stanford, CA (US); THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 257 days.

(21) Appl. No.: 17/251,605

(22) PCT Filed: Jun. 27, 2019

(86) PCT No.: PCT/US2019/039541
§ 371 (c)(1),
(2) Date: Dec. 11, 2020

(87) PCT Pub. No.: WO2020/006255
PCT Pub. Date: Jan. 2, 2020

(65) Prior Publication Data
US 2021/0244659 A1 Aug. 12, 2021

Related U.S. Application Data

(60) Provisional application No. 62/690,737, filed on Jun. 27, 2018.

(51) Int. Cl.
*A61K 9/00* (2006.01)
*A61F 2/14* (2006.01)
*A61K 9/06* (2006.01)
*A61K 47/10* (2017.01)
*A61K 47/36* (2006.01)
*A61K 47/42* (2017.01)

(52) U.S. Cl.
CPC ............ *A61K 9/0051* (2013.01); *A61F 2/142* (2013.01); *A61K 9/06* (2013.01); *A61K 47/10* (2013.01); *A61K 47/36* (2013.01); *A61K 47/42* (2013.01); *A61F 2210/0076* (2013.01)

(58) Field of Classification Search
CPC ........ A61K 9/0051; A61K 9/06; A61K 47/10; A61K 47/36; A61K 47/42; A61F 2/142; A61F 2210/0076
See application file for complete search history.

(56) References Cited

U.S. PATENT DOCUMENTS

| | | | | |
|---|---|---|---|---|
| 5,522,888 A | * | 6/1996 | Civerchia | B29D 11/00009 623/6.59 |
| 2011/0087274 A1 | * | 4/2011 | Sargeant | A61L 31/145 606/213 |
| 2015/0183988 A1 | | 7/2015 | Becker et al. | |
| 2017/0189581 A1 | * | 7/2017 | Desai | C07D 237/26 |
| 2018/0371117 A1 | * | 12/2018 | Anseth | C08G 65/48 |

FOREIGN PATENT DOCUMENTS

| | | | | |
|---|---|---|---|---|
| WO | WO2007/001926 | | 1/2007 | |
| WO | WO-2007001926 A2 | * | 1/2007 | ............. A61K 47/34 |
| WO | WO-2017165389 A2 | * | 9/2017 | ......... C08B 37/0084 |
| WO | WO2017176779 | | 10/2017 | |
| WO | WO-2017176779 A1 | * | 10/2017 | ............. A61K 35/30 |
| WO | WO-2017182483 A1 | * | 10/2017 | ............. A61K 47/58 |

* cited by examiner

*Primary Examiner* — Doan T Phan
(74) *Attorney, Agent, or Firm* — Pamela J. Sherwood; Bozicevic, Field & Francis LLP

(57) ABSTRACT

Compositions and methods are provided for lamellar and defect reconstruction of corneal stromal tissue using biomaterials that form a defined gel structure in situ. Such gels can serve as cellular or acellular lamellar substitutes to reconstruct corneal stroma, facilitate matrix remodeling, and support multilayered re-epithelialization of wounded corneal stromal tissue, as well delivery vehicles for cells, biomolecules, and/or pharmaceutical agents to wound sites throughout the body.

4 Claims, 12 Drawing Sheets

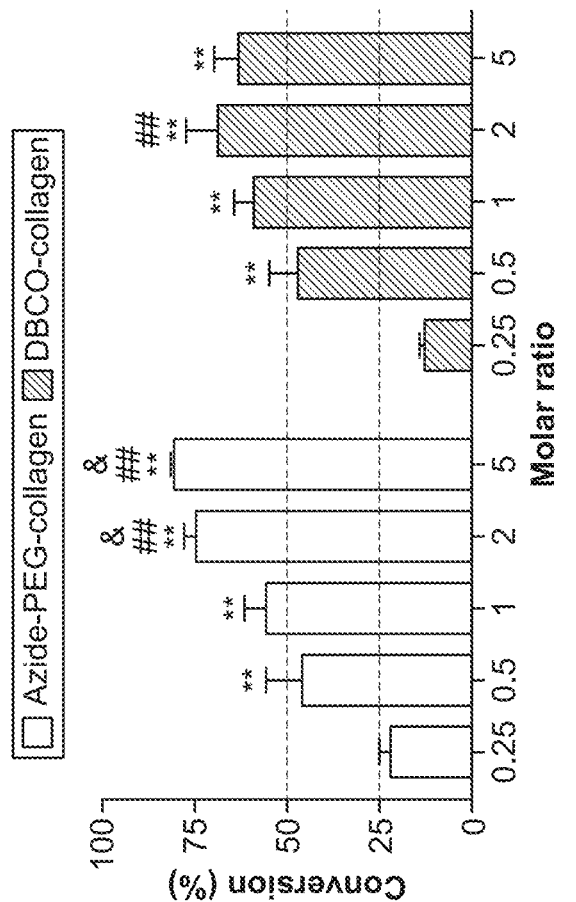
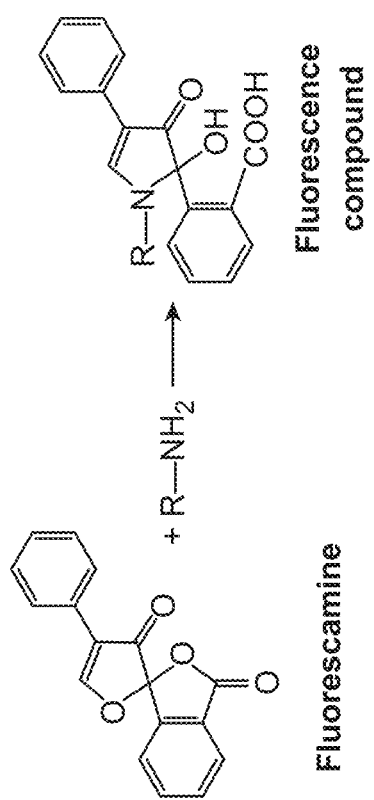
FIG. 2A
FIG. 2B

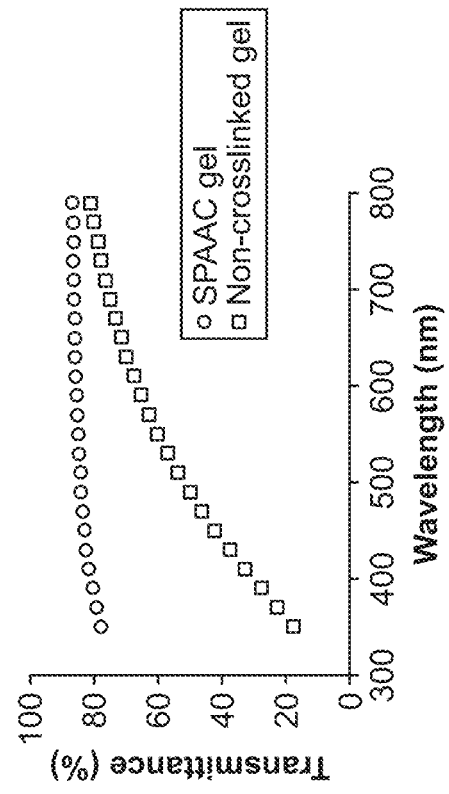
FIG. 3A
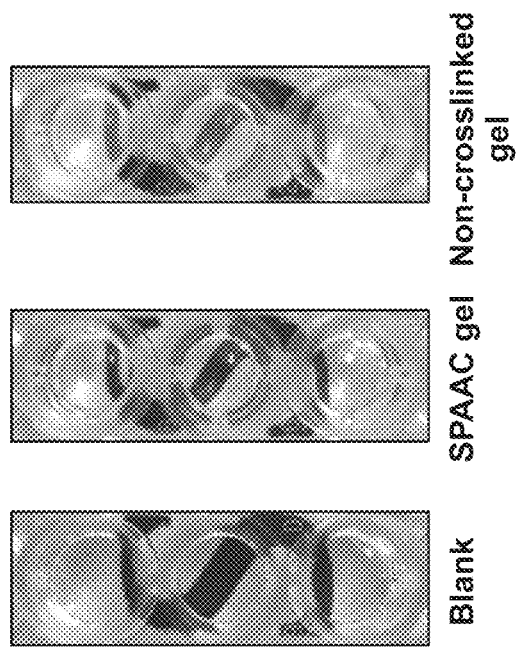
FIG. 3C
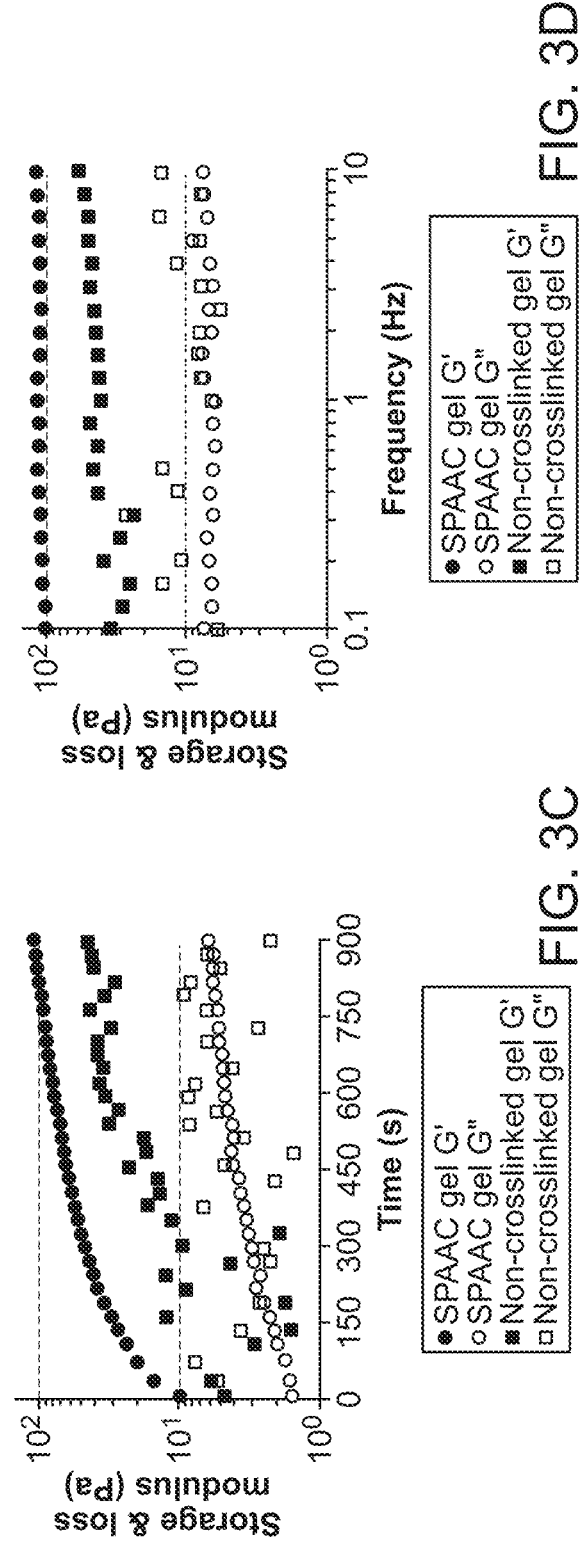
FIG. 3B
FIG. 3D

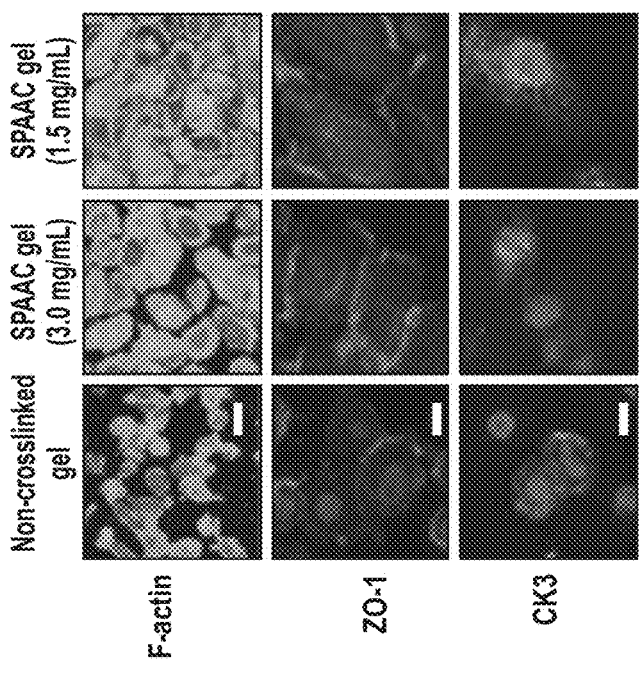
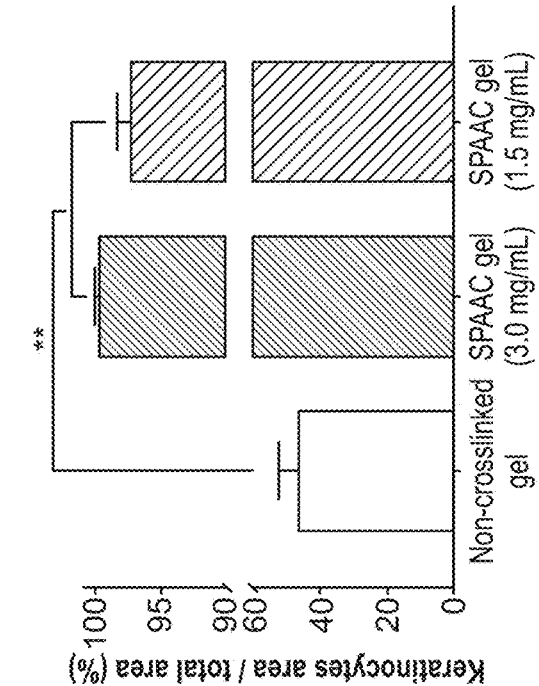
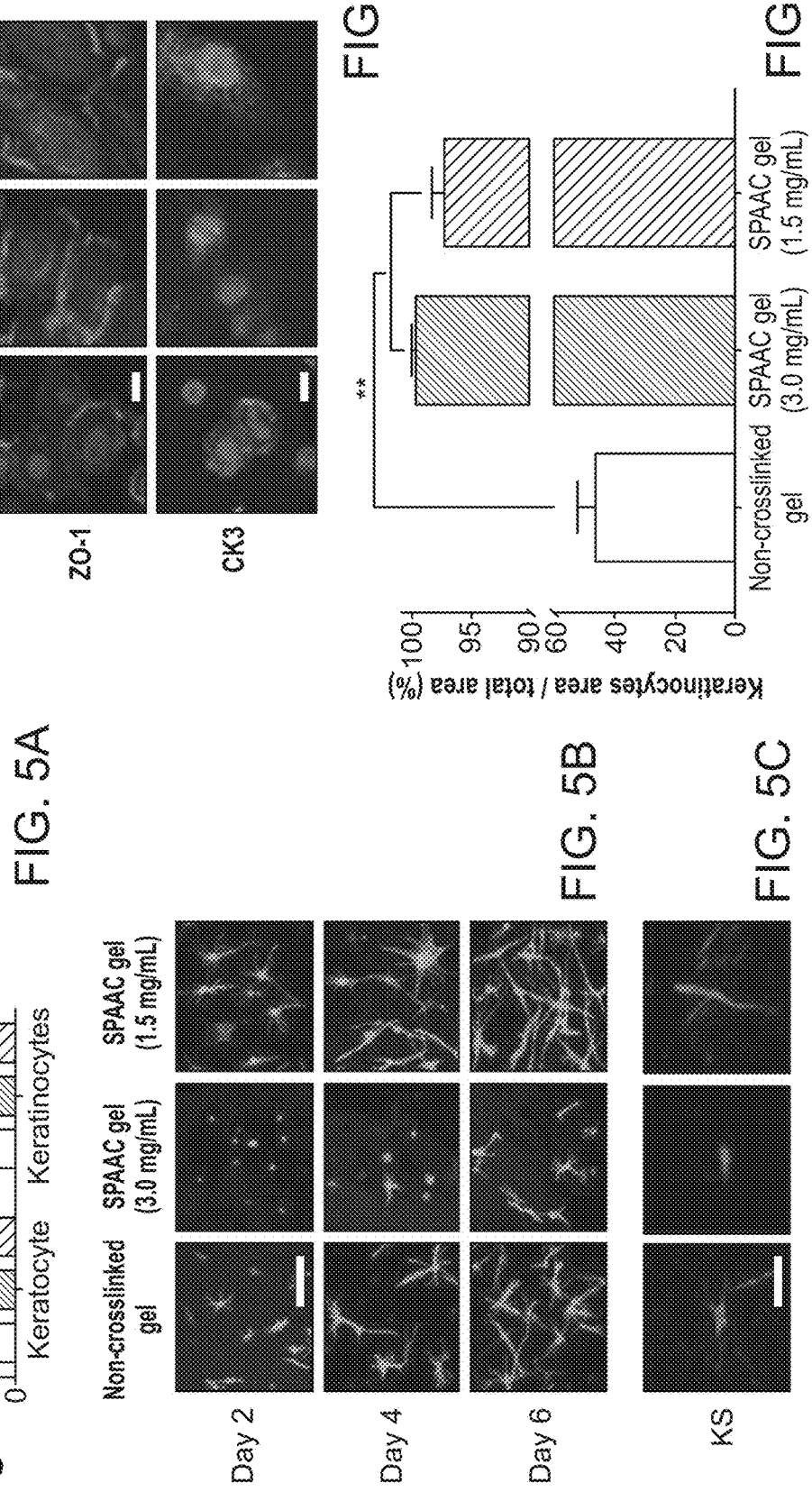
FIG. 5A
FIG. 5B
FIG. 5C
FIG. 5D
FIG. 5E

COMPOSITIONS AND METHODS FOR IN SITU-FORMING TISSUE CONSTRUCTS

CROSS REFERENCE

This application claims the benefit of and is a 371 of PCT Application No. PCT/US2019/039541, filed Jun. 27, 2019, which claims benefit of U.S. Provisional Application No. 62/690,737, filed Jun. 27, 2018 which is incorporated herein by reference in their entireties.

STATEMENT OF GOVERNMENT SUPPORT

This invention was made with Government support under contract EY028176 awarded by the National Institutes of Health. The Government has certain rights in the invention.

TECHNICAL FIELD

Methods are provided for tissue reconstruction using in-situ formed constructs, and in particular to the reconstruction of ocular tissue using corneal constructs that form defined hydrogel structures in-situ.

BACKGROUND

Corneal transplantation has evolved substantially in the past two decades, and, depending on the indication, can now be done in a number of different ways. The advent of lamellar and endothelial keratoplasty, where only certain layers of the cornea are replaced, has narrowed the number of cases where a full-thickness penetrating keratoplasty is required. Although these procedures are done through variable thickness cadaveric allograft corneas, the availability of donor tissue remains limited in most parts of the world.

An alternative approach that has garnered interest is the creation of multi-layered graft materials. Decellularized allograft and xenografts have been tested with some success. For instance, a construct comprised of recombinant human collagen type III crosslinked by carbodiimide chemistry has shown promising results as a synthetic lamellar graft with remodeling of the matrix and a resulting structure similar to normal corneal tissue.

To date, these approaches require the formation and molding of the replacement button ex vivo, and the placement within a deep anterior lamellar cavity created within the cornea. Yet there remain clinical situations such as a deep ulcer and/or severe thinning where corneal stromal integrity has been severely compromised, and surgical intervention with a tectonic graft remains the only option, albeit of last resort. Pre-formed, bioengineered corneal buttons would be difficult to place within an irregularly shaped corneal stromal ulcer and may not be mechanically stable enough to merit lamellar or full-thickness excision of diseased corneal tissue.

There is an unfilled need for effective in-situ forming methodologies and compositions to non-invasively fill, stabilize and regenerate deep corneal wounds, particularly in patients where the risks and morbidities associated with penetrating the globe are high.

SUMMARY

Compositions, kits and methods are provided for use as in-situ forming tissue constructs, also referred to as a defined hydrogel structure, that can be cellularized to aid in wound healing and tissue regeneration, particularly in repair, regeneration, and/or reconstruction of lamellar or partial defects of wounded corneal tissue. The compositions, kits and methods also find use in the repair, regeneration, and/or reconstruction of skin, subcutaneous tissue, nerve, muscle, bone, cartilage, vitreous, tendon, ligament, fat, retinal, conjunctival, scleral, cardiac, adrenal, and other types of tissue.

The invention provides a flowable biomaterial composition comprising a biopolymer and/or polymer such as a structural biomolecules, e.g. proteins, polysaccharides, glycosaminoglycans, glycoproteins, e.g. collagenm hyaluronic acid, alginate, cellulose, chitosan, chondroitin sulfate, dextran; PEG, multi-arm PEG, poloxamers, etc., and combinations thereof, in which the biopolymer has been modified to form a defined hydrogel structure at a site of application. In some embodiments the polymer is collagen, hyaluronic acid, or a combination thereof.

In an embodiment, a flowable biomaterial composition for use as an in-situ-forming corneal construct, i.e. a defined hydrogel structure, is provided, which finds use in treating or reconstructing a surgically incised or wounded corneal area in a mammalian subject in need thereof. The flowable biomaterial may comprise cells or therapeutic agents, or both, that aid in treating or reconstructing a surgically incised or wounded area, where the cells or agent are entrapped or encapsulated in the defined hydrogel structure. Cells of interest include regenerative cells, such as a stem cell, including without limitation corneal stem cells. Cells suitable for treating corneal tissue may include, for example, one or more of corneal stromal stem cells, mesenchymal cells, keratocytes, keratinocytes, endothelial cells, and epithelial cells, and limbal epithelial cells, and transient amplifying cells.

In some embodiments the biopolymers are linked to form the hydrogel structure through covalent bonds (cross-links), including without limitation through bio-orthogonal chemistries, such as chemistries based on strain-promoted azide-alkyne cycloaddition (SPAAC) and chemistries based on inverse electron demand Diels-Alder (IED-DA) reaction, as well as other "click"-type reactions such as thiol-ene reactions and hydrazone ligation. For such covalent chemistries the flowable biomaterial composition may be provided as two solutions that react and cross-link at the site of application under ambient conditions on a tissue surface without the need for an external stimulus such as light.

In one embodiment an in-situ forming tissue construct i.e. a defined hydrogel structure, is formed by combining reactants at the tissue site for covalent cross-linking, for example by copper-free click chemistry. For example, a first composition comprising a biopolymer that is functionalized with azide reactive groups, and a second composition comprising a biopolymer that is functionalized with alkyne reactive groups, such as dibenzocyclooctyne (DBCO) or bicyclooctyne, are combined. Upon consecutive or simultaneous administration to the desired site, e.g. a corneal area, and direct contacting of each other, the reactants undergo cross-linking and gelation via strain-promoted azide-alkyne cycloaddition (SPAAC), to form a defined hydrogel structure, on the site in situ, wherein the defined hydrogel structure is effective in treating or reconstructing the wounded area. Azide groups and/or alkyne groups are optionally attached to biopolymers through a spacer arm, e.g. polyethylene glycol. In other embodiments, these groups comprise the end-functionality of PEG molecules with two or more arms (e.g. 3 or 4 or more arms). Non-limiting examples include a collagen-azide solution combined with multi-arm PEG-alkyne solution, which forms a covalently linked hydrogel.

Other bio-orthogonal chemistries include, but are not limited to 1,3 dipolar cycloadditions, copper-catalyzed azide-alkyne cycloaddition reactions, Diels-Alder, inverse-electron demand Diels-Alder, Staudinger ligation, and nitrile oxide cycloaddition (see Madl/Heilshorn review in Adv Functional Materials page 4). In some cases, such as copper-catalyzed azide-alkyne cycloaddition reactions, a chelating agent may be needed to address and remove free copper ions.

Other "click" type chemistries that can also be used in this invention include conjugate addition such as thiol-maleimide, thiol vinyl-sulfone, photomediated thiol-ene, hydrazone bonds, oxime ligation, and maleimide-furan Diels-Alder.

In some embodiments multi-arm molecules, e.g. multi-arm PEG which include, for example, 2, 3, 4, or 8-arm PEG molecules modified with alkyne, such as bicyclo[6.1.0] nonyne (BCN), etc., are used to crosslink a biopolymer, including without limitation azide-functionalized collagen, to form in-situ forming hydrogels. The use of the multi-arm PEG allows the stiffness of the resulting hydrogel to be tuned, where increased numbers of arms result in a stiffer hydrogel, and different molecular weights fo the PEG molecule (and arm length) lead to different properties.

In another aspect, a method of treating or reconstructing a surgically incised or wounded corneal site in a mammalian subject is provided, by administering a flowable biomaterial that forms a defined hydrogel structure at the site under ambient conditions without the need for an external stimulus such as light. The defined hydrogel structure is effective in treating or reconstructing the wounded corneal area. In some embodiments the flowable biomaterial is applied to an existing cavity, which can be highly irregular in shape, e.g. a pathologic cavity such as an ulcer. In some embodiments a cavity is debrided to eliminate necrotic material and create fresh wound edges. In some embodiments a cavity of specific shape and dimensions created, e.g. with surgical instruments, or a laser, for example to remove tissue that is scarred, fibrotic, opacified, etc.

In another aspect, the flowable biomaterial, or a defined hydrogel structure derived therefrom as described above, is provided, which optionally comprises cells, therapeutic agents, etc. The cytocompatible hydrogel structure is suitable for use in tissue repair or regeneration.

In yet another aspect, the instant disclosure includes a kit for making a corneal construct for use in treating or reconstructing a surgically incised or wounded corneal area in a mammalian subject. A kit will comprise a flowable biomaterial that forms a defined hydrogel structure at the site under ambient conditions without the need for an external stimulus such as light. The defined hydrogel is effective in treating or reconstructing a wounded corneal area. The flowable biomaterial may be provided as a single composition, or may be provided as two compositions in separate containers. For example, a first composition comprising a polymer that is functionalized with azide reactive groups, and a second composition comprising a polymer or biopolymer that is functionalized with alkyne reactive groups, such as dibenzocyclooctyne (DBCO) or bicyclooctyne (BCN) may be provided.

The gels in the present invention can serve as, but not be limited to, tissue scaffolds, tissue substitutes, optical elements (e.g. corneal or lens tissue), tissue fillers, tissue spacers, or as delivery vehicles for cells, tissues, and/or pharmaceutical agents.

These and other embodiments of the subject invention will readily occur to those of skill in the art in view of the disclosure herein.

BRIEF DESCRIPTION OF THE FIGURES

FIG. 2 illustrates the efficiency of collagen conjugation. (Panel A) Fluorescamine reacts with free amines and allows for the quantification of collagen conjugation conversion. (Panel B) Conversion of collagen's free amines to functionalized PEG or DBCO groups dependent on the molar ratio of NHS reagent:amine. The statistical analysis was performed between molar ratios in each group (azide or DBCO). The symbols of *, #, and & were used for representing significant difference to 0.25, 0.5, and 1-fold molar ratio, respectively. The significant differences were represented by $0.01<p<0.05$ (*, #, and &) and $p<0.01$ (**, ##, and &&).

FIG. 3 illustrates physical properties of chemically crosslinked collagen gels by SPAAC in comparison to non-covalently crosslinked collagen gels. (Panel A) Photographic images of blank and collagen gels inside of 96 well plates. (Panel B) Transmittance spectra of collagen gels from 350 to 800 nm. (Panel C) Dynamic moduli of collagen gels as a function of time during gelation. The gels were mounted immediately after mixing. (Panel D) Dynamic moduli of collagen gels as a function of frequency. G' and G" represent storage and loss modulus, respectively.

FIG. 5 illustrates the viability and morphology of keratocytes and keratinocytes in SPAAC-crosslinked gels in comparison to non-covalently crosslinked gels. (Panel A) Viability of keratocytes encapsulated in and keratinocytes seeded on non-crosslinked and SPAAC collagen gels after six days in culture. (Panel B) F-actin staining (green) showing the morphology of keratocytes encapsulated in SPAAC-crosslinked gels and non-crosslinked collagen gels at day 2, 4, and 6. Scale bar: 200 μm. (Panel C) Keratocytes encapsulated in the SPAAC-crosslinked gels and non-crosslinked gels produced keratan sulfate (KS, red) at day 6. Scale bar: 50 μm. (Panel D) F-actin (green) staining and expression of ZO-1 (red) and CK3 (green) of keratinocytes seeded on non-crosslinked and SPAAC gels. Scale bar of F-actin staining image: 100 μm. Scale bars of ZO-1 and CK3 staining images represent 20 μm. (Panel E) The keratinocyte coverage areas that were divided by total area after 2 days in culture (**$p<0.01$). The nucleus (blue) was stained for both keratocytes and keratinocytes.

(FIG. 10A) Immunofluorescence images showing expression of alpha-smooth muscle actin (alpha-SMA, orange) but not keratan sulfate in corneal stromal stem cells (CSSCs) encapsulated within non-covalently crosslinked collagen gels, indicating differentiation into a myofibroblastic phenotype. When the same CSSCs are encapsulated within SPAAC-crosslinked collagen gels, they express keratan sulfate (red) without alpha-SMA, indicative of differentiation into keratocytes. Scale bar (all 4 images): 20 µm Blue stain=DAPI. (FIG. 10B) mRNA analysis of encapsulated CSSCs within collagen gels shows that gels with 100% of the collagen modified to enable covalent crosslinking (i.e., no unconjugated collagen) express the highest levels of ALDH3A1, while maintaining HGF and KGF expression.

DETAILED DESCRIPTION

Figure 1:
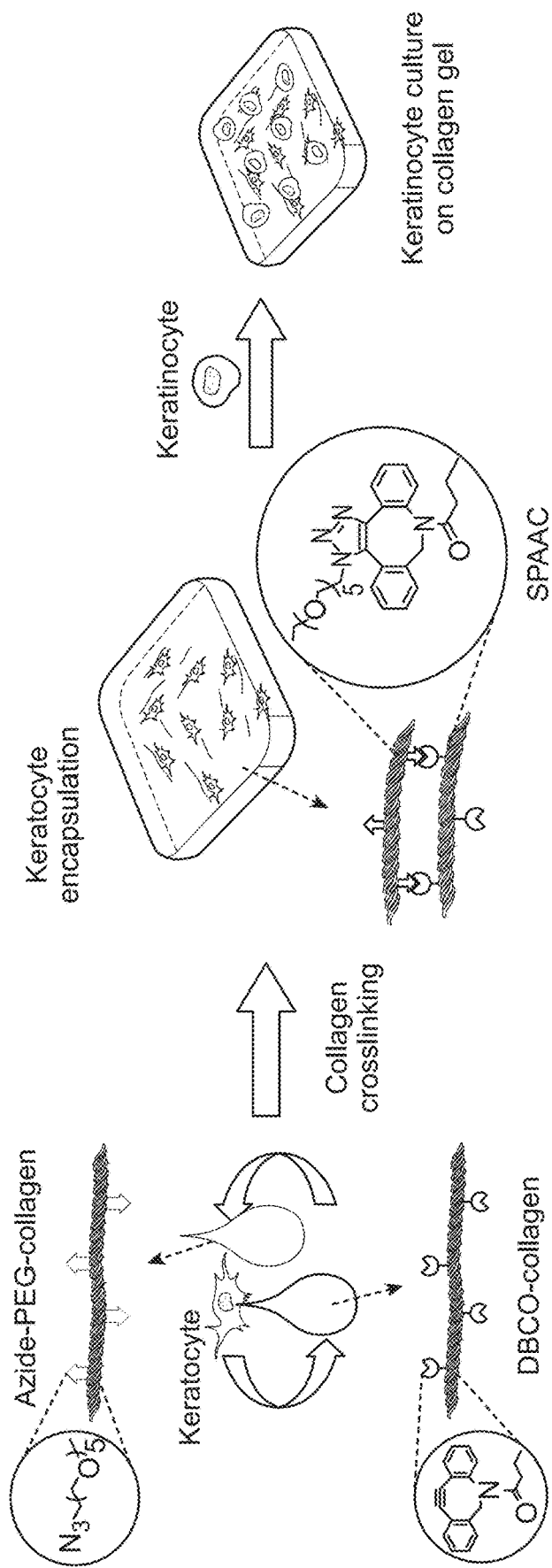
FIG. 1 is an illustration of crosslinked collagen gel matrix formation by strain-promoted azide-alkyne cycloaddition (SPAAC). Azide-PEG-conjugated collagen (Azide-PEG-collagen) and DBCO-conjugated collagen (DBCO-collagen) were mixed with keratocytes to fabricate a corneal stroma tissue substitute. Keratinocytes were seeded on the keratocyte-encapsulated collagen gel to confirm the formation of the epithelial layer.
Figure 4A:
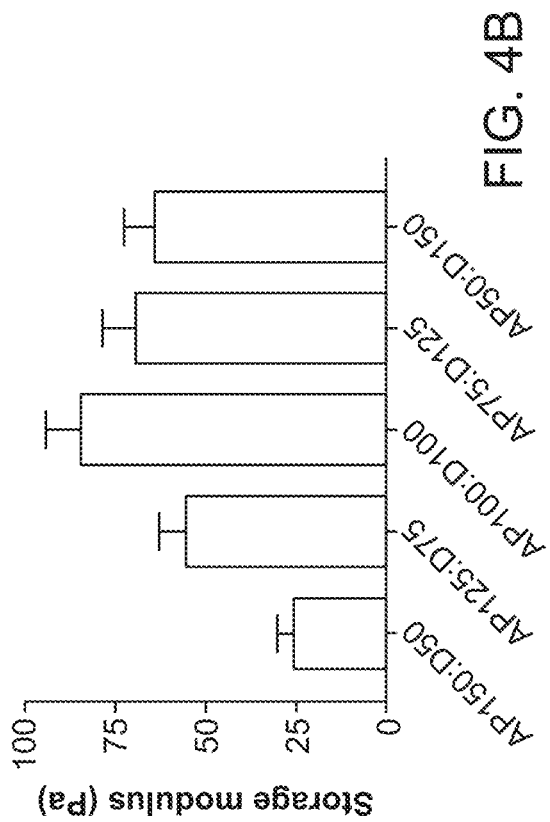
FIG. 4 displays mechanical properties of SPAAC-crosslinked gels, as shown by their storage moduli. (Panel A) Storage moduli depending on ratio of azide:DBCO (collagen concentration: 3 mg/mL) as a function of frequency after gelation. The numbers with 'AP' and 'D' represent the ratios of azide-PEG-collagen and DBCO-collagen, respectively. (Panel B) Average storage moduli depending on the ratio of azide:DBCO from 0.1 to 10 Hz of frequency. (Panel C) Storage moduli depending on collagen concentration as a function of frequency after gelation, where the ratio of azide:DBCO functionalized collagen was 1:1. (Panel D) Average storage moduli as a function of collagen concentration.
Figure 4B:
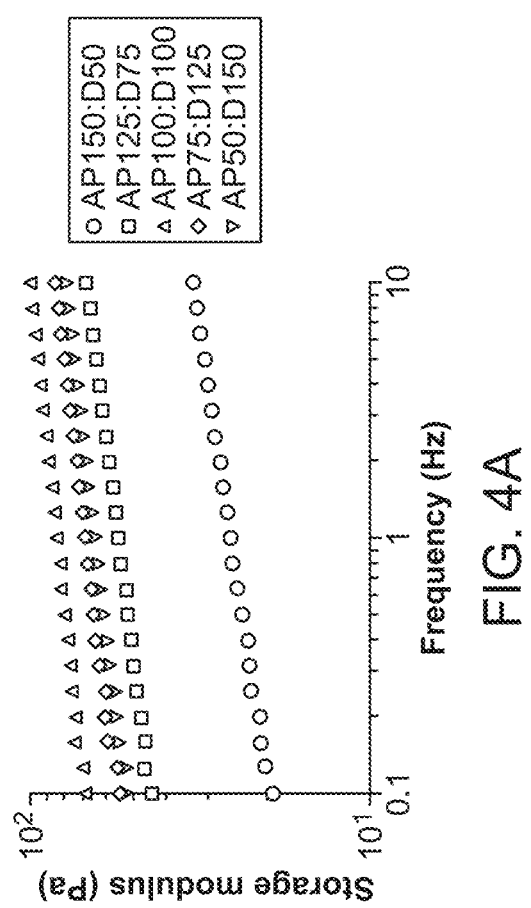
Figure 4C:
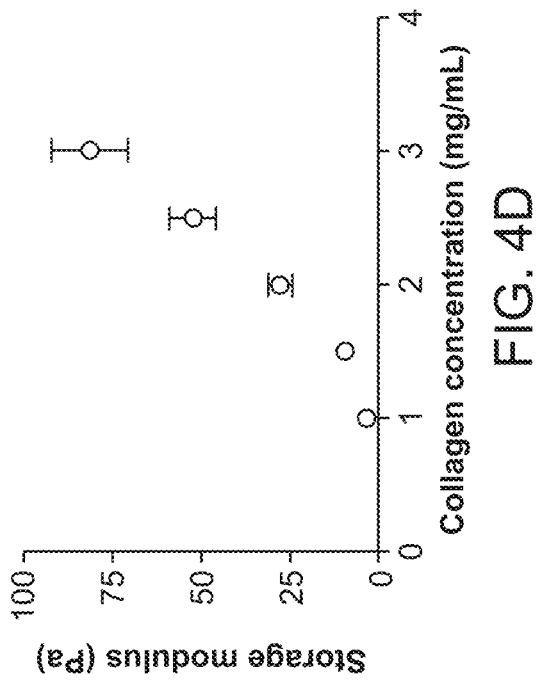
Figure 4D:
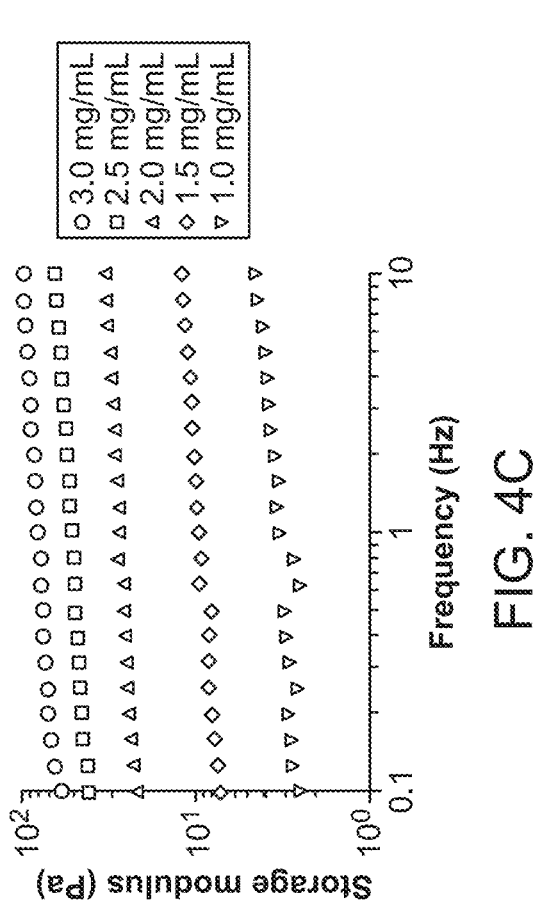

The invention described below relates to injectable precursor compositions and methods for in-situ forming tissue constructs that find use in partial or total repair, regeneration, and/or reconstruction of wounded tissue in a mammalian subject or host organism. Other purposes of the instant disclosure include, but are not limited to, the use for effective transplantation of cells into the host organism to encourage recellularization of wounded tissue, the delivery of bioactive agents, biomolecules, and/or pharmaceutical agents (either singular or combinations of agents/molecules), and the use as a tissue model for the in-vitro study of cellular responses and interplay.

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting. Although a number of methods and materials similar or equivalent to those described herein can be used in the practice of the present invention, the preferred materials and methods are described herein.

In describing embodiments of the present invention, the following terms will be employed, and are intended to be defined as indicated below. As used in this specification and the appended claims, the singular forms "a," "an" and "the" include plural referents unless the content clearly dictates otherwise.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The practice of the present invention will employ, unless otherwise indicated, conventional methods of medicine, pharmacology, chemistry, biochemistry, molecular biology and recombinant DNA techniques, within the skill of the art. Such techniques are explained fully in the literature. See, e.g. S. S. Wong and D. Jameson Chemistry of Protein and Nucleic Acid Cross-Linking and Conjugation (CRC Press, 2Supnd/Sup edition, 2011); G. T. Hermanson Bioconjugate Techniques (Academic Press, 3Suprd/Sup edition, 2013); B. Bowling Kanski's Ophthalmology: A Systematic Approach. 8e (Saunders Ltd., 8Supth/Sup edition, 2015); A. L. Lehninger, Biochemistry (Worth Publishers, Inc., current addition). All publications, patents and patent applications cited herein, whether supra or infra, are hereby incorporated by reference in their entireties.

As used herein, "about" or "approximately" mean within 50 percent, preferably within 20 percent, more preferably within 5 percent, of a given value or range.

A value which is "substantially different" from another value can mean that there is a statistically significant difference between the two values. Any suitable statistical method known in the art can be used to evaluate whether differences are significant or not.

"Statistically significant" difference means a significance is determined at a confidence interval of at least 90%, more preferably at a 95% confidence interval.

The terms "treatment," "treating," "treat," and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease.

The terms "reconstructing" and "reconstruction," and the like are used herein to generally refer to rebuilding, healing and regenerating an injured matter or tissue.

The term "subject" or "mammalian subject" refers to any mammalian subject for whom treatment or therapy is desired, particularly humans. "Mammal" for purposes of treatment refers to any animal classified as a mammal, including humans, domestic and farm animals, and zoo, sports, or pet animals, such as non-human primates, dogs, horses, cats, cows, sheep, goats, pigs, camels, etc. In some embodiments, the mammal is a human.

The term "therapeutically effective amount" or "effective amount" means the amount of a compound, agent, composition, construct that when administered to a mammalian subject for treatment is sufficient, in combination with another agent, or alone in one or more doses or administrations, to effect such treatment for the disease. The "therapeutically effective amount" will vary depending on the compound, agent, composition, construct, the defect or disease to be treated, and its severity and the age, weight, etc., of the mammalian subject to be treated.

As used herein, the term "cell" in the context of the in-vivo and in-vitro applications of the present invention encompasses mammalian cells of any genus or species. The types of cells that may be incorporated into the polymeric biomaterial include progenitor cells of the same type as those from the tissue site, and progenitor cells that are histologically different from those of the tissue site such as embryogenic or adult stem cells, that can act to accelerate the healing, regenerative or reconstructive process. The compositions comprising cells can be administered in the form of a solution or a suspension of the cells mixed with the polymeric biomaterial solution, such that the cells are substantially immobilized within the application site upon gelation. This serves to concentrate the effect of the cells at the site of application; and may provide for release of the cells over a course of time.

Somatic stem cells are characterized as cells with the ability to self-renew and give rise to differentiated progeny via mitosis. These adult stem cells are often found in specialized locations, or niches, in tissues throughout the body. When tissue is damaged, stem cell populations are often instrumental in replacing the lost cells to restore tissue function and integrity. Stem cells are found in many different tissues, including hematopoietic stem cells in the bone marrow, muscle, adipose tissue, skin, umbilical cord blood, neural tissue, etc. and may be isolated from tissues, or can be differentiated in vitro from pluripotent stem cells. Corneal cells may used, for example limbal epithelial stem cells, cornea stromal stem cells, keratinocytes, keratocytes, endothelial cells, etc. may be isolated, harvested, and/or propagated from cadeveric donor corneal tissue, from small limbal biopsies from patients (either autologous from one's healthy eye, or from another living patient's eye as a donation); generated by in vitro culture, etc.

In the cornea, stem cells include limbal epithelial stem cells (LESCs), which may be found at the limbal region that marks the transition zone between cornea and conjunctiva. Keratin expression is distinct in these limbal basal cells, with a lack of cytokeratins CK3 and CK12, and expression of CK14/CK59-11, The cells are also positive for adult stem cell marker ABCG2. ABCB5, a member of the ATP-binding cassette family of proteins, has also been identified as a definitive LESC marker. Expansion of limbal cells in vitro and transplantation to central cornea can restore epithelial function.

Corneal stem cells also include corneal stromal stem cells, which are quiescent, mesenchymal cells. It has been suggested that corneal stromal stem cells are a subpopulation of stromal cells that can differentiate into keratocytes. Stromal corneal stem cells are also positive for ABCG2 expression.

For in vivo application, the polymeric compositions and cells can be mixed and then applied to the in vivo site. The cells are preferably added to the polymeric compositions immediately prior to administration to the application site to enhance survival of living cells. The cells of the thus resulting cellularized hydrogel may maintain a cellular phenotype at the site of application, which is usually the affected, i.e. damaged, area for at least one day, one week, or one month following application. Where the polymeric composition is administered in a two solution format, it can be crosslinked in situ for tissue repair or regeneration.

Therapeutically effective amounts of the cells encapsulated within a hydrogel of the instant disclosure will vary depending e.g., on the condition to be treated, typical survival of the particular cell type within the hydrogel construct (e.g., including the average lifespan of cells of the particular cell type), etc.

In some embodiments, a therapeutically effective amount of cells is $1\times10^3$ or more cells, including e.g., $5\times10^3$ or more, $1\times10^4$ or more, $5\times10^4$ or more, $1\times10^5$ or more, $5\times10^5$ or more, $1\times10^6$ or more, $5\times10^6$ or more, $1\times10^7$ or more. $5\times10^7$ or more, $1\times10^8$ or more, $5\times10^8$ or more, $1\times10^9$ or more, $5\times10^9$ or more, $1\times10^{10}$ or more, $5\times10^{10}$ or more. Alternatively, the hydrogel, following administration of the polymeric compositions and crosslinking at the site of application, can also be seeded with cells and used to repair and regenerate damaged corneal or generally ophthalmic tissue.

The defined hydrogel structure provides a three-dimensional construct for new cell growth. The hydrogels of the present invention can be used not only for the encapsulation of cells, but also for the encapsulation of other molecules and agents that may enhance proper remodeling of the crosslinked polymer so that its contents are replaced with the matrix elements native to the surrounding tissue (e.g. in the cornea, the crosslinked matrix is eventually broken down and replaced by normal conical tissue).

As used herein, the term "under physiological conditions" encompasses those conditions that are compatible with living cells, e.g., predominantly aqueous conditions of a temperature, pH, salinity, osmolarity, osmolality etc.

The term "gel" or "hydrogel," as used herein, refers to a crosslinked network of hydrophilic biopolymers. Hydrogels of the instant disclosure will generally be made by combining a first flowable composition containing reactive groups of one nature and a second flowable composition containing reactive groups of a different nature, and possibly more flowable compositions with reactive groups of further different nature. The flowable compositions may be combined in situ, particularly where the network is covalently linked.

The term "biopolymer" refers to a biocompatible polymers comprising polymers that can be found naturally in organisms, as well as chemical and physical modifications of such polymers, and include, but are not limited to, proteins, fibrins, fibrinogen, collagens, gelatins, elastins, lamnin, fibronectin, extracellular matrix constituents, glycosaminoglycans, chondroitin sulfate, keratan sulfate, dermatan sulfate, heparan sulfate, hyaluronic acid, albumin, alginates, chitosans, cellulose, thrombin, heparin, polysaccharides, synthetic polyamino acids, prolamines, combinations thereof, and other such molecules.

Naturally occurring polymers include, but are not limited to, proteins and carbohydrates. The term "bio-polymer" also includes derivatised forms of the naturally occurring polymers that have been modified to facilitate cross-linking to a synthetic polymer of the invention. Additionally, the term "bio-polymer," as used herein, includes proteins produced using recombinant methodologies, such as, for example, recombinant collagen.

Combinations of biopolymers can be used, to form compositions such as an interpenetrating polymer network, semi-interpenetrating polymer networks, or copolymer networks. Combinations may be combined in different ratios, e.g. where two biopolymers are used, a ratio may be 1:50; 1:10, 1:5, 1:3, 1:2, 1:1; 2:1; 3:1; 5:1; 10:1; 50:1; etc. For example, collagen can be crosslinked in the presence of uncrosslinked hyaluronic acid and/or chondroitin sulfate to form a semi-interpenetrating polymer network of collagen and hyaluronic acid (and/or chondroitin sulfate). In another embodiment, hyaluronic acid can be crosslinked in the presence of collagen to form a semi-interpenetrating polymer network. In another embodiment, collagen and hyaluronic acid can be crosslinked to each other to form a copolymeric network. In still another embodiment, collagen can be crosslinked in an independent process from the crosslinking of hyaluronic acid (either simultaneously or in sequence) to yield a fully interpenetrating polymer network.

In preparing hydrogels in accordance with the present invention, the ratio of polymers containing reactive groups of one nature and polymers containing reactive groups of a different nature to each other can range from about 0.1 to about 3.0, from about 0.7 to about 3.0, from about 1.0 to about 2.0, from about 0.1 to about 10, or from about 0.5 to about 5.0.

When used as tissue constructs in tissue engineering for replacing or restoring tissue and organ function, as contemplated herein, hydrogels of the present invention may contain mammalian cells, such as stem cells such as corneal stromal stem cells, or somatic cells such as keratocytes and keratinocytes, in order to repair tissue or to promote tissue repair, reconstruction and regeneration. The hydrogels of the present invention can be prepared with enhanced mechanical as well as structural properties and resistance to degradation, can be made visually transparent and because of their cytocompatibility support cell overgrowth, in-growth and encapsulation of cells.

A hydrogel in accordance with the present invention comprises an assembly of polymers and is suitable for use in a variety of applications, including, but not limited to, clinical, therapeutic, prophylactic, or cosmetic applications. The hydrogel material can be used to replace, restore, and/or augment tissue and/or organ function in a mammalian subject in need thereof. Various biomedical, biotechnological, and/or pharmaceutical applications include, for example, corneal substitutes, therapeutic lenses, cell and/or drug delivery carriers, and tissue engineering scaffolds. Besides benefitting therapeutically in the treatment of a disease, disorder or traumatic injury of an eye and, and enhancing corneal regeneration and reconstruction, hydrogels in accordance with the present invention can be used in ophthalmic devices to enhance optical power or comfort.

Hydrogels that form in situ are adaptable to complicated defect sites when compared to structurally preformed hydrogels. With structures that form in situ and which are contemplated herein, two or more solutions containing the macromeric, precursor compositions of the hydrogel are injected or otherwise delivered to the site where the hydrogel is to be used and crosslinking is initiated. The precursor compositions can be manipulated and formed when the crosslinked solution is over a strain threshold. In most cases, the hydrogel does not require a catalyst to crosslink, thus avoiding biocompatibility problems. The precursor materials are substantially bioorthogonal and will crosslink in the presence of gelatins, collegens, lipids, carbohydrates or polymer nanofibers. Because of their crosslinking reaction kinetics, the hydrogels of the present invention can encapsulate and transport highly sensitive cells and other biological additives. Moreover, many of the hydrogels of the present invention have no known toxic byproducts.

Polymeric hydrogels can be defined as two- or multicomponent systems consisting of a three-dimensional network of polymer chains, and water that fills the space between macromolecules. A hydrogel is a network of polymer chains that are water-soluble, sometimes found as a colloidal gel where water is the dispersion medium. Hydrogels are superabsorbent (they can contain over 99% water) natural or synthetic polymers. Hydrogels possess also a degree of flexibility that is very similar to natural tissue, due to their considerable water content. Two general classes of hydrogels are known in the art. There are physical hydrogels, where the chains are connected by electrostatic forces, hydrogen bonds, hydrophobic interactions or chain entanglements. Physical crosslinking of polymer chains can be achieved using a variety of environmental triggers (pH, temperature, ionic strength) and a variety of physicochemical interactions (hydrophobic interactions, charge condensation, hydrogen bonding), e.g. those gels are prone to temperature changes and usually transform to polymer solutions at particular temperatures. Chemical hydrogels generally have covalent bonds linking the chains. Chemical methods include various click reactions, thiol-ene additions, metal-catalyzed azide-alkyne cycloadditions, Michael additions and Diels-Alder reactions. Metal-free, strain-promoted azide-alkyne "click" cycloaddition reactions have been applied to cell imaging as well as hydrogels systems due to its highly efficient conversion, orthogonality, and bio-friendly characteristics. The gel formation process is atom neutral in that there are not residuals that contaminate the system and could pose toxicity problems to associated biological systems.

As used herein, the term "reactive group" means a molecule or molecular moiety within one composition that specifically reacts with another reactive moiety in another composition under physiological conditions and, when brought into sufficient proximity under appropriate conditions, is able to link the two molecules or moieties by a chemical bond, e.g., a covalent bond. Reactant groups of interest are usually involved in bioorthogonal chemistry, i.e. chemical reactions that can occur inside of living systems without interfering with native biochemical processes. The reaction must be selective between endogenous functional groups to avoid side reactions with biological compounds, and have to be non-toxic and must function in biological conditions taking into account pH, aqueous environments, and temperature.

In general, the methods of the invention utilize compositions of modified biopolymers that react with each other to form stable hydrogel structures. Biopolymers for these purposes have been modified by the addition of reactive groups.

In one embodiment, reactive groups are copper-free click chemistry reactants, which form covalent bonds upon mixing. See Click Chemistry: Diverse Chemical Function from a Few Good Reactions Hartmuth C. Kolb, M. G. Finn, K.

Barry Sharpless Angewandte Chemie International Edition Volume 40, 2001, P. 2004, herein specifically incorporated by reference). Copper-free click chemistry is an alternative approach to traditional click chemistry that proceeds at a lower activation barrier and is free of cytotoxic transition metal catalysts. The absence of exogenous metal catalysts makes these reactions suitable for the in vivo applications. Strain-promoted alkyne-azide cycloaddition reaction (SPAAC) is a form of copper-free click chemistry that involves the reaction between an strained alkyne and an azide.

Other click chemistry reactions of interest include, for example, the use of copper-catalyzed azide-alkyne cycloaddition reaction (CuAAC) in applications where the toxicity of copper is not important. Alternatively the inverse-demand Diels Alder ligation pair trans-cyclooctene-tetrazine (TCO-Tz) may be used. The chemoselective TCO-Tz ligation pairs possess ultrafast kinetics (>800 $M^{-1}s^{-1}$), selectivity, and long-term aqueous stability are advantages of TCO-Tz.

In such an embodiment, biopolymers, which may be the same or different, are modified to comprise reactive groups, where a first reactive group is an azide group and a second reactive group is a cycloalkyne group. The reacting, i.e. contacting, step results in a reaction between the azide group of the azide-modified biopolymer and the cycloalkyne group of the cycloalkyne-modified biopolymer, thereby synthetically and covalently modifying both biomolecules so that a hydrogel forms in-situ, i.e. at the site where the contacting occurs, upon the reacting step. Reactive groups of interest, include, but are not limited to, thiols, alkyne, a cyclooctyne, an azide, phosphine, a maleimide, an alkoxy amine, an aldehyde, a thiol, a methacrylate or acrylate, and protected versions thereof, and precursors thereof.

When two different biomolecules are used as conjugated pairs, for instance, if collagen is azide-modified, and HA is alkyne-modified (or vice-versa), when they are mixed, a covalently crosslinked co-polymer network of collagen and HA is formed through SPAAC-mediated linkages between the pendant azides and alkynes. Biomolecules may also be crosslinked with non-biological macromolecules such as PEG and multi-arm PEG, with compatible end groups. For instance, an azide-modified collagen can be crosslinked with a multi-arm PEG with alkyne endgroups (e.g. BCN or DECO). In another example, an alkyne-modified collagen can be crosslinked with a multi-arm PEG with azide endgroups. The multi-arm PEG may have two, three, four, or more arms, including 8 arms, with some or all of the end groups being functionalized with a moiety that promotes chemical crosslinking with SPAAC. The multi-arm PEG may have two, three, four, or more arms, including 8 arms, with some or all of the end groups being functionalized with a moiety that promotes cross-linking. More than 8 arms may be used as well, for instance to dendrimeric-type polymers with multiple arms and branches.

In addition, interpenetrating polymer networks can be formed, where one network is crosslinked via bioorthogonal crosslinking chemistry (e.g. SPAAC, Diels Alder, inverse electron demand Diels Alder, etc.) while the other is formed via another chemistry. The two networks can be formed by two different bio-orthogonal reactions (e.g. SPAAC and inverse electron demand Diels Alder). Semi-interpenetrating polymer networks can also be formed where one species is not crosslinked at ail, such in a case where an HA network is formed by chemical crosslinks around a solution of linear/uncrosslinked collagen. Similar, a collagen network can be formed by chemical crosslinks around a solution of linear/uncrosslinked HA.

The term "biocompatible" refers to the absence of stimulation of a severe or escalating biological response towards administration of a composition, and is distinguished from a mild, transient inflammation which typically accompanies surgery or implantation of foreign objects into a living organism.

The term "polymer," as used herein, refers to a molecule consisting of individual monomers joined together. Polymers that are contemplated herein can be naturally occurring, synthetically produced, or produced using recombinant methodologies.

The term "transparent," as used herein, refers to at least 70%, 80, or 90% transmission of white light.

The term "D1300," as used herein means a strained cyclooctyne molecule dibenzylcyclooctyne.

The term "DCN," as used herein in means a strained cyclooctyne molecule, bicyclo[6.1.0]nonyne.

Polyethylene glycol chains of various lengths can be used as spacers within the functionalization process, wherein the first end of the polyethylene glycol chain is covalently linked on one side to a reactive group (or groups), as defined herein, including a PEG azide or a monofunctional or PEG cyclooctyne.

Precursor Compositions that In Situ Gelate and Form Tissue Constructs Upon Cross-Linking Using bioconjugation methodologies including bioorthogonal copper-free click chemistry methods such as the Strain Promoted Azide Alkyne Cycloaddition (SPAAC), tissue constructs may be formed in-situ, meaning at the site of application which is usually the site of injury, wound or defect, by reactions between at least two (a "first" and a "second") polymeric "precursor" compositions. Those precursor compositions are functionalized with reactive groups as described herein, which include without limitation multiple azide reactive groups in a first composition and with multiple alkyne reactive groups in a second composition. The precursor groups may be separately administered to the site of tissue injury, wound or defect. Reaction of the groups results in gelation of the combined precursor compositions to form a defined hydrogel composition at the site of injury, wound or defect. Spacers comprising polyethylene glycol (PEG) in various lengths may be used in the functionalization process. Such polymeric precursor compositions are typically flowable biomaterials.

The precursor compositions of the present invention encompass biocompatible biopolymers such as collagen that can be functionalized with reactive groups and that form hydrogels in situ upon reaction. Such in-situ gelling compositions that are functionalized with different reactive groups are applied to a site of injury, wound or damage, for example to the site of a corneal defect, and undergo a sol-gel (liquid to solid) transformation at the site of the injury, wound or defect, and so form a tissue construct upon the site of injury, wound or defect.

The pharmaceutically acceptable excipients, such as vehicles, adjuvants, carriers or diluents, are readily available. Moreover, pharmaceutically acceptable auxiliary substances, such as pH adjusting and buffering agents, tonicity adjusting agents, stabilizers, wetting agents and the like, are readily available.

Polymers contemplated for use in the instant disclosure as exemplary hydrogel-forming molecules include glycoproteins, carbohydrates, and other macromolecules, including, but not limited to, various types of collagen, proteins, fibrins, fibrinogen, collagens, gelatins, elastins, laminin, fibronectin, extracellular matrix constituents, glycosaminoglycans, hylauronic add, albumin, alginates, chitosans, cellulose, thrombin, heparin, polysaccharides, synthetic polyamino acids, prolamines, hydroxy methylcellulose, chitosan, combinations thereof, and other such molecules, including recombinant versions of such polymers.

Collagen, a widely used biomaterial for producing tissue scaffolds and constructs, is the major constituent of the extracellular matrix, and has been used as wound dressing, corneal shields, and engineered corneal matrix. It is well known that collagen's molecular structure plays a crucial role in cell adhesion, migration, and differentiation.

In various embodiments of the present invention in order to demonstrate the utility of the described precursor compositions to form in-situ a tissue construct at the site of a corneal defect, bovine type-I collagen was employed as matrix due to its low immunogenicity compared to other collagen types. Collagen type I is commonly used as a cellular scaffold in three-dimensional cell culture because collagen gel matrices are more similar to the native cell environment than general two-dimensional cell culture dishes. When an acidic collagen solution is neutralized and incubated at 20-37° C., the collagen forms a gel through fibril formation. However, collagen extracted from tissue loses its original fibril density and three dimensional architecture, and as a result, neutralized non-covalently crosslinked collagen gels have low mechanical strength.

The physical properties of collagen can be modulated by crosslinking techniques that enhance mechanical strength, enzymatic degradation resistance, and transparency. For example, transparency of crosslinked biomaterials such as SPAAC-crosslinked collagen gels is an important aspect for their usefulness in corneal applications. Whereas physically collagen gels exhibit optical turbidity in proportion to the degree of randomly organized fibrillar structures in the collagen, crosslinked gels are optically clear because of the presumably reduced random organization of fibrillar structures through crosslinking.

Hyaluronic acid is another polymer of interest, which may be used alone or in combination with collagen. It is a polymer of disaccharides, themselves composed of D-glucuronic acid and N-acetyl-D-glucosamine, linked via alternating $\beta$-(1→4) and $\beta$-(1→3) glycosidic bonds. Polymers of hyaluronic acid can range in size from 5,000 to 20,000,000 Da in vivo. The average molecular weight in human synovial fluid is 3-4 million Da, and hyaluronic acid purified from human umbilical cord is 3,140,000 Da. Hyaluronic acid is energetically stable, in part because of the stereochemistry of its component disaccharides. Bulky groups on each sugar molecule are in sterically favored positions, whereas the smaller hydrogens assume the less-favorable axial positions.

Cellularized or Acellular Compositions

For each type of tissue being replaced, the flowable biomaterial compositions can be injected with cells, i.e. cellularized, or without cells, i.e. acellular. Such cells can be somatic/differentiated cells, induced pluripotent stem cells, or progenitor/stem cells.

The in-situ encapsulation of corneal keratocytes within gels to support corneal re-epithelialization was investigated in SPAAC-crosslinked versus non-covalently crosslinked gels. To mimic the structure of the cornea which is composed of a multi-layered epithelium of keratinocytes overlying a stromal layer of collagen type I and keratocytes, keratinocytes were cultured on collagen gels with encapsulated keratocytes, whereby the collagen was either crosslinked by SPAAC or without additional covalent crosslinking. Cell behavior, phenotype, and cytocompatibility of encapsulated keratocytes were evaluated as a function of crosslinking and mechanical properties. Corneal keratinocytes were cultured on the SPAAC-crosslinked gel and were able to adhere and migrate over the surface (shown in FIG. 1)

All collagen gels were cytocompatible with both cell types, but the cells showed different phenotypic behavior depending on the type of gel. SPAAC-crosslinked gels supported a more favorable and stable keratinocyte morphology on their surface than non-crosslinked gels likely as a result of more optimal substrate stiffness, gel integrity, and resistance to degradation.

As described herein, such in-situ formed constructs or scaffolds are able to support a co-culture of keratocytes within their matrix and keratinocytes on their surface, and can be provided as cellular or acellular lamellar substitutes to facilitate multilayered re-epithelialization of wounded corneal stromal tissue. In addition, such scaffolds provide a three-dimensional in-vitro model system for studying keratocyte-keratinocytes interactions within corneal tissue.

Crosslinking Via Strain-Promoted Azide-Alkyne Cycloaddition (SPAAC)

In one embodiment of the invention, a bio-orthogonal approach based on bioorthogonal chemistry, that can make highly specific covalent bonds without interfering with cells and biomolecules in a living system, is used to crosslink biopolymer matrices with strain-promoted azide-alkyne cycloaddition for encapsulating cells or for carrying out reactions on ocular wound sites including corneal defects. Strain-promoted azide-alkyne cycloaddition (SPAAC) is a bio-orthogonal, copper-free form of click chemistry and suitable to chemically crosslink polymer or biopolymers such as collagen around cultured cells, including corneal stromal stem cells or keratocytes (in-situ encapsulation). SPAAC can be used to form covalent bonds between biomolecules in the presence of living cells.

To facilitate strain-promoted azide-alkyne cycloaddition (SPAAC) mediated crosslinking in embodiments of the present invention, collagen was functionalized with either azide or dibenzocyclooctyne (DBCO) reactive groups using N-hydroxysuccinimide (NHS) coupling chemistry. A poly (ethylene glycol) (PEG) spacer was introduced in the azide group conjugation to allow for enhanced conjugation efficiency.

In contrast to commonly used chemical crosslinking agents such as glutaraldehyde, carbodiimide, and N-hydroxysuccinimide (NHS) which may be cytotoxic due to unselective reactions with cells, azides and alkynes do not react with functional groups present on cells and tissues, and only proceed with the cycloaddition reaction when they encounter each other. SPAAC reaction produces no free radicals and side products, can proceed in water under ambient conditions without the need for external catalysts such as an initiator or copper, and do not need for a trigger such as light or heat.

SPAAC can be performed under ambient conditions in aqueous solution without the need for solvents or catalysts, produces no side reactions or free radicals or side products, and does not react with surrounding cells, proteins, or tissue. Because of these numerous advantages, SPAAC was used in the various embodiments of the present invention to crosslink collagen and encapsulate cells.

Methods

In some aspects of the invention, methods are provided for treating an injury, wound or defect that requires tissue regeneration, tissue replacement or repair, regeneration, and/or reconstruction of ocular, skin, subcutaneous tissue, nerve, muscle, bone, cartilage, vitreous, tendon, ligament, fat, retinal, conjunctival, scleral, cardiac, adrenal, and other types of tissue. In these methods, flowable biomaterials are applied to a site of injury, wound or defect where, upon crosslinking of reactive groups, a defined hydrogel structure tissue construct is formed in-situ on top of the injury, wound or defect, which serves to regenerate, reconstruct and repair the tissue injury, wound, or defect.

Utility

The injectable flowable biomaterial compositions and methods of the present invention can be applied to any clinical situation where tissue engineering, regeneration or reconstruction in a mammalian host or subject is necessary. Tissue engineering is a rapidly growing field encompassing a number of technologies aimed at replacing or restoring tissue and organ function. The key objective in tissue engineering is the regeneration of a defective tissue through the use of materials that can integrate into the existing tissue so as to restore normal tissue function. Such injectable compositions can comprise cells that settle in the host and encourage recellularization of the wounded tissue. Furthermore, such injectable compositions can also serve as a three-dimensional tissue model for the in-vitro study of cellular responses and interplay.

Application as In-Situ Forming Hydrogel Upon Ocular Defects

To address an unfilled need for effective compositions and methodologies to treat and regenerate ocular defects, including corneal defects, precursor compositions are described in various examples herein that upon crosslinking form in-situ corneal constructs on top of corneal defects. Such ocular and corneal defects may be caused by, e.g., neurotrophic keratopathy, recurrent cornea erosion, corneal ulcer, corneal burns, exposure keratopathy, physical trauma, retinal disease, retinal degeneration, optic nerve damage, optic nerve degeneration, and other disorders.

The cornea is a highly specialized transparent tissue and, as the most anterior ocular tissue, protects the eye by acting as a physical barrier. It is comprised of three cellular layers: the outer layer being the stratified squamous corneal epithelium, the center layer being the corneal stroma, and the inner layer being the corneal endothelium. The corneal stroma makes up the majority of the corneal tissue. The extracellular matrix (ECM) of the corneal stroma has a lamellar, highly organized structure that facilitates the transparency of the cornea, whereby each lamella is composed of tightly organized collagen fibrils. Keratocytes are mesenchymal-derived cells that are quiescent in the mature cornea and that are arranged within the corneal stroma. Upon injury to the cornea, the keratocytes become activated, and several changes in the corneal stroma occur. Upon an initial apoptotic phase, keratocytes lose their quiescence, start to divide and develop either into phenotypes that start to secrete extracellular matrix for corneal regeneration or into phenotypes that induce fibrotic scar formation at the site of injury. Unlike in uninjured stromal tissue, the extracellular matrix in scar tissue is disorganized and opaque, and may seriously impair visual acuity and lead to blindness.

Delivering (cultured) cells such as corneal stromal stem cells (CSSCs) or keratocytes to the site of corneal injury may minimize the fibrotic response and enhance the regeneration of the corneal tissue. Delivery of corneal cells, such as keratocytes and keratinocytes, and other cells, within injectable polymeric precursor compositions that gel in-situ upon cross-linking, as described herein, may be instrumental in repairing and regenerating corneal tissue. The cells can then be encapsulated into the corneal construct to provide a scaffold for proliferation and reepithelialization of the corneal defect.

Such compositions may comprise functionalized biopolymers such as collagen (type I) that are crosslinked in situ, and where the crosslinking transforms the injectable precursor compositions into a substantially transparent hydrogel that serves as a corneal stromal scaffold, substitute or construct on top of a corneal or stromal defect, wound or wounded area to enhance the regenerative capacity of the cornea to restore viable corneal tissue.

Such polymer-based precursor compositions, when functionalized with azide-alkyne crosslinking agents and which can additionally contain a suspension of corneal keratocytes to aid in the reepithelization of the wounded corneal area, are consecutively applied as flowable precursor compositions to a wounded corneal area, and then gelated on the spot (in situ) by SPAAC crosslinking to produce an in situ-forming corneal stromal scaffold which is kept in place on top of the wound site. The in situ-formed scaffold mimics the thickness and smooth, continuous surface of the cornea.

In examples described herein, the polymer-based composition was collagen that was modified with azide and dibenzocyclooctyne (DBCO) or bicyclooctyne (BCN) groups to enable the SPAAC reaction between azide-conjugated collagen and alkyne-conjugated (DBCO-conjugated or BCN-conjugated) collagen. An equivalent ratio between azide and cyclooctyne groups led to high efficiency in collagen crosslinking with increasing modulus. The ratios and concentrations of conjugated collagens were adjusted to obtain a range of mechanical properties of the resulting collagen gels.

In-Situ Molding

In embodiments of the present invention, the crosslinked gel can be applied with or without cells, and with or without an overlying contact lens (hard or soft lens) which can be used as an in situ mold to create the desired contour and curvature of the crosslinked gel on the ocular surface. This in situ molding process may be important for bestowing the desired refractive power to the surface of the cornea, since the air-cornea interface is responsible for most of the refractive power of the eye. By providing a smooth, transparent, and properly curved surface to the central cornea, the gel can restore vision to patients whose vision was severely compromised by a central defect or ulcer. Furthermore, the gel can be applied to any part of the cornea (central, paracentral, or peripheral cornea), and can be used to encapsulate stromal cells, epithelial cells, limbal cells, or combinations thereof. In other embodiments, the eyelids can be sutured shut (i.e. tarsorraphy can be placed) completely or partially to create a protective environment for the eye after the gel is placed. This can be done with or without a contact lens in place over the cornea and applied gel.

Application as In-Situ Forming Hydrogel Upon Other Defects

The compositions and methods of the present invention can be configured to a range of applications to facilitate tissue regeneration (e.g., bone or muscle formation) or to replace tissues such as adipose tissue (e.g., in cosmetic or reconstructive surgeries), blood vessels and valves (e.g., in angioplasty, vessel inflammation, or valve deterioration), or skin (e.g., in cases of skin damage due to heat, mechanical force or by disease). As such, the compositions and methods of the present invention find use for the repair, regeneration, and/or reconstruction of skin, subcutaneous tissue, nerve, muscle, bone, cartilage, vitreous, tendon, ligament, fat, retinal, conjunctival, scleral, cardiac, adrenal, and other types of tissue. Such repair, regeneration, and/or reconstruction may also be necessary following injuries that may be associated with or result from ischemia, infections, inflammations, auto-immune reactions, organ failures, fibrosis, periodontal diseases, and can concern tissues of solid organs, e.g., kidney, liver, large intestine, small intestine, skeletal muscle, heart, pancreas, lung.

Kits

The present invention also provides kits comprising separate containers holding compositions comprising polymers, such as collagen, hyaluronic acid, etc., that are functionalized with azide groups, and polymers that are functionalized with alkyne groups, and optionally with spacer arm(s) bridging the azide or alkyne groups to the polymer, and optionally admixed with living cells or biomolecules (e.g. proteins) or pharmaceutical agents or combinations thereof to be delivered to the wounded tissue site.

Compositions can be in liquid form or can be lyophilized. Suitable containers for the compositions include, for example, bottles, vials, syringes, and test tubes. Containers can be formed from a variety of materials, including glass or plastic.

The kit can further comprise a container comprising pharmaceutically acceptable excipients or formulating solutions such as buffers, diluents, filters, needles, and syringes or other delivery devices. The kit can also comprise a package insert containing written instructions describing methods for care of a corneal wound as described herein.

Administration

The precursor flowable biomaterial compositions of the present invention can be administered in the form of pharmaceutical compositions, comprising an isotonic excipient prepared under sufficiently sterile conditions for administration to a mammalian subject, particularly to a human being. In certain embodiments, multiple cycles of treatment may be administered by repeatedly applying the precursor compositions to the site of injury, wound or defect for a time period sufficient to effect at least a partial healing of the injury, wound or defect, or, preferably, for a time period sufficient to effect a complete healing of the injury, wound or defect.

Experimental Procedures

The following methods and materials were used in the examples that are described further below.

Materials

Unless otherwise noted, all chemicals and solvents were of analytical grade and used as provided by the manufacturer. Dibenzocyclooctyne-sulfo-N-hydroxysuccinimidyl ester (DBCO-sulfo-NHS), collagenase, dimethyl sulfoxide (DMSO), fluorescamine, sodium hydroxide solution (1.0 N), bovine serum albumin (BSA), fibronectin, agar, Cholera Subunit A, insulin, Triton-X, anti-chondroitin sulfate antibody, anti-keratan sulfate antibody, trypan blue solution, and Cell counting kit-8 were purchased from Sigma-Aldrich (St. Louis, MO, USA). Phosphate-buffered saline (PBS) pH 7.4, 10×PBS, Slide-A-Lyzer dialysis kit (3.5 k MWCO), collagen I bovine protein solution (5 mg/mL), collagenase, epidermal growth factor recombinant human protein (EGF), Dulbecco's modified eagle medium/nutrient mixture F-12 (DMEM/F-12) with 4-(2-hydroxyethyl)-1-piperazineethanesulfonic acid (HEPES), fetal bovine serum (FBS), streptomycin sulfate, insulin-transferrin-selenium (ITS), Dulbecco's phosphate-buffered saline (DPBS), antibiotic-antimycotic, 1% horse serum, L-glutamine, keratinocyte-serum free media (KSFM), bovine pyruvate extract (BPE), trypsin, Live/Dead viability/cytotoxicity staining kit, paraformaldehyde (PFA), 5% normal goat serum, Alexa Fluor 647 Protein Labeling Kit, Alexa Fluor Phalloidin 488, Alexa Fluor 488 secondary antibody, and Alexa Fluor 546 secondary antibody were purchased from Thermo Fisher Scientific (Waltham, MA, USA). Azido-poly(ethylene glycol)$_5$-N-hydroxysuccinimidyl ester (azide-PEG-NHS) was purchased from BroadPharm (San Diego, CA, USA).

Collagen conjugation and characterization. Type I bovine collagen was first pH neutralized using a solution of 1.0 M sodium hydroxide solution, deionized (DI) water, and 10×PBS in a 3:57:20 ratio. The 5 mg/mL collagen solution was mixed with the neutralization solution in 3:2 ratio so that the final concentration of collagen was 3 mg/mL. Azide and DBCO functional groups were conjugated to the neutralized collagen using NHS chemistry to react with collagen's primary amines. For the azide conjugation (azide-PEG-collagen), azide-PEG-NHS was dissolved in DMSO to a concentration of 100 mg/mL, and 0.25, 0.5, 2, and 5-fold molar ratios were used for conjugation. For the DBCO conjugation (DBCO-collagen), DBCO-sulfo-NHS was dissolved in PBS to 100 mg/mL, and the same molar ratios were used. The collagen and NHS reagent mixed solutions were incubated for 2 hr at 4° C. Azide-PEG-conjugated collagen was dialyzed via Slide-A-Lyzer dialysis kit overnight at 4° C. in PBS, and DBCO-conjugated collagen was used immediately after incubation without dialysis.

The conjugation efficacy was evaluated by fluorescamine assay. Fluorescamine was dissolved in DMSO to a concentration of 3 mg/mL, and then 25 μL of the fluorescamine solution was added to 75 μL of conjugated collagen. After 30 min incubation at room temperature, the fluorescence intensity (Ex/Em=380/470 nm) was measured using a SpectraMax M Series Multi-Mode Microplate Reader (Sunnyvale, CA, USA). The conjugation efficiency was evaluated based on the concentration calculated from the standard curve of an unmodified collagen solution. Briefly, the fluorescence intensities of collagen solutions from 0.08 to 5 mg/mL were measured with the above procedure, and the intensity measurements showed a linear correlation with collagen concentration. From the linear standard curve, the concentration was evaluated from the measured intensity, and the conversion was estimated.

In all following experiments, collagen was functionalized with a 2-fold molar ratio of NHS reagents.

Collagen gel formation. A 1:1 v/v mixture of azide-PEG-collagen and DBCO-collagen were mixed to form crosslinked collagen gel by SPAAC reaction (SPAAC gel) and incubated for 30 min at 37° C. The azide-collagen and DBCO-collagen were diluted before mixing to fabricate SPAAC gels that had different concentrations. For non-covalently crosslinked gels, the collagen was neutralized as we mentioned above and incubated for 30 min at 37° C. according to the collagen gelation procedure of Thermo Fisher Scientific protocol, which is physically entangled collagen gel commonly used for cell culture.

Optical property characterization of collagen gels. The gels' absorbance from 350 to 800 nm was measured using a SpectraMax M Series Multi-Mode Microplate Reader. The SPAAC gel (1.5 mg/mL) and non-covalently crosslinked gel were fabricated in a 96 well plate, and the volume was 100 μL. The absorbance was converted to transmittance using the relation ($A=2-\log_{10}$ (% T)).

Mechanical property characterization of collagen gels. The mechanical properties of the collagen gels were evaluated using an ARES-G2 rheometer (TA Instruments, New Castle, DE, USA) at Stanford Soft & Hybrid Materials Facility (SMF, Stanford, CA, USA). For the non-crosslinked gel, neutralized collagen was mounted on the plate and measured. For the SPAAC gels, azide-PEG-conjugated collagen and DBCO-conjugated collagen were mixed and mounted on the 25 mm stainless steel plate. To determine gelation time, time sweeps were performed at room temperature for 15 min at 1% strain and 1 Hz oscillatory frequency. Then frequency sweeps from 0.1 to 10 Hz with a fixed 1% strain were performed to determine the completion of gelation.

To evaluate how the mechanical properties of the gels could be modulated, the azide-PEG:DBCO ratio and the conjugated collagen concentrations were adjusted systematically. To ensure complete gelation, the resultant solutions were incubated at room temperature for 2 hr, and then frequency sweeps from 0.1 to 10 Hz with a fixed 1% strain were performed.

Isolation of corneal cells. Primary corneal stromal cells (keratocytes) were obtained from rabbit and human corneas following previously published protocols. The cells were grown in a 75 $cm^2$ flask in medium containing 1% horse serum and used at passage one. Keratinocytes were grown in KSFM medium containing BPE and EGF. After reaching confluency, the cells were subcultured and used at passage two. Corneal stromal stem cells were grown in MEM containing 10% FBS and used before passage ten Cytotoxicity, morphology, and phenotype of keratocytes/keratinocytes encapsulated and seeded within collagen gels. Prior to encapsulation, keratocytes were removed from culture flasks by trypsinization, pelleted by centrifugation, and resuspended in DMEM/F-12 containing 1% of horse serum. Cells were pelleted once again, then the supernatant was removed and approximately $10^4$ cells were resuspended in azide-PEG-collagen. Next, DBCO-collagen was added to the cell suspension in a 1:1 volumetric ratio. To compare the effect of collagen concentration on cell behaviors, 1.5 and 3.0 mg/mL conjugated collagens were used. The gels were crosslinked at 37° C. for 30 min and then the appropriate cell medium was added so that the gels were submerged. The culture medium was changed every two days. The same procedure described above was used to remove keratinocytes from the flask. Then, keratinocytes were seeded on top of SPAAC and non-covalently crosslinked collagen gels that had been previously incubated with medium (KSFM, with BPE and EGF). At day six cell viability was assessed via Live/Dead staining, following the manufacturer's instructions. The number of viable and dead cells was determined using Image J software. Cell viability was obtained by dividing the number of live cells by the number of total cells. Each condition was performed in triplicate and averaged from three distinct experiments.

To determine cell phenotype and morphology, keratocytes and keratinocytes were encapsulated in and cultured on top of the collagen gels as described above, respectively. Then, after day 2, 4 and 6, cells were fixed with 4% PFA for 15 min. After washing with PBS, the wells were blocked, and the cells were permeabilized for 30 min with 5% normal goat serum and 0.5% Triton-X. Next, Alexa Fluor Phalloidin 488 (1:40) was added for 30 min or the cells were incubated overnight with primary antibodies, including anti-keratan sulfate (1:50), ZO-1 (1:100) and CK3 (1:100). After washing three times with PBS, secondary antibodies (1:1000), Alexa Fluor 488 and 546, were added for 2 hr. Finally, after washing with PBS, DAPI was added for 5 min in PBS solution (1:1000). The cells were mounted, and the cell morphology and phenotype were observed using confocal microscopy (ZEISS LSM 880, Carl Zeiss Ag, Oberkochen, Germany).

Co-culture of human keratocytes and keratinocytes within collagen matrix gels. Human keratocytes were encapsulated in SPAAC (1.5 and 3.0 mg/mL) and non-covalently cross-linked collagen gels following the description above. Then, keratinocytes were seeded on the gels, as described above. KSFM medium with supplements was used to culture both of the cells. At day 6, the medium was removed, and the cells were fixed and stained with Phalloidin 488 and DAPI. The cells were mounted and both cells morphology within the gel was observed using confocal microscopy.

Phenotype of corneal stromal stem cells encapsulated within collagen gels. Prior to encapsulation, CSSCs were removed from culture flasks by trypsinization, pelleted by centrifugation, and resuspended in DMEM/F-12 containing ITS. Cells were pelleted once again, then the supernatant was removed and approximately $10^6$ cells/mL cells were resuspended in azide-PEG-collagen. Next, DBCO-collagen was added to the cell suspension in a 1:1 volumetric ratio. The gels were crosslinked at 37° C. for 30 min and then the appropriate cell medium was added so that the gels were submerged. Cells were fixed and stained as described above using anti-keratan sulfate (1:50) and alpha smooth muscle actin (1:100).

To determine the expression of keratocyte specific markers and growth factors, corneal stromal stem cells were encapsulated in SPAAC-crosslinked collagen gels as described above. The crosslinking density was modulated by blending in different amounts of unmodified collagen, where "none" is non-covalently-crosslinked collagen, "medium" is a 1:1:1 ration of azide-collagen:DBCO-collagen:unmodified collagen, and "high" is 1:1 azide-collagen:DBCO-collagen. Gels were formed as above, and kept in culture for one week. Then the gels were enzymatically degraded using collagenase and the cells were pelleted an collected from quantitative polymerase chain reaction (qPCR). RNA was isolated using a RNeasy kit (Qiagen) protocol and then reversed transcribed using iScript cDNA synthesis kit (Bio-Rad) following the manufacturer's protocol. For qPCR using the TaqMan gene expression assay, 100 ng of the resulting cDNA was used in preparing the PCR reaction mixtures following the manufacturer's protocol (ThermoFisher).

Lamellar keratectomy in ex vivo rabbit corneas. Fresh rabbit eyes were obtained from Vision Tech and disinfected with 10% povidone-iodine solution. The globe at the equator was wrapped and tied with a sterile gauze to increase the intraocular pressure and provide a firm corneal surface to make a wound. A three-step anterior lamellar keratectomy was performed under a stereo microscopy (VistaVision™, VWR, Radnor, PA, USA). Firstly, an 8-mm diameter keratectomy groove of consistent depth was created by a biopsy punch (Miltec, Inc., Oak Creek, WI, USA). Then the globe was untied to decrease the intraocular pressure and soften the ocular surface. Secondly, A 27-gauge needle was injected into the posterior stroma and used to manually dissect the posterior stroma. Lastly, using a freehand technique, approximately 150-200 μm of the anterior stroma including epithelial layer was removed using a crescent blade.

The air/liquid organ culture system used in this study was modified from previous reports. Following wounding, the injured corneas were excised from the globes with a 1-mm scleral rim, grasping only scleral rims and not the clear cornea. Excised corneas were immediately transferred onto individual pre-formed agar plugs to maintain normal culture and nutritional support. Agar plugs were made from 1:1 mixtures of serum-free medium containing double strength antibiotics, and 2% agar in distilled water. The agar plugs were made within polydimethylsiloxane (PDMS) molds. The base part and curing agent of Sylgard 184 (Dow corning, Midland, MI, USA) were mixed as 10:1 weight ratio, and the 10 mL round bottom tubes were posted to the PDMS precuring mixture. The tubes were removed after PDMS curing, and the PDMS mold was autoclaved before use. Wounded corneas on the agar plugs were placed in a 12 well plate with 1 mL of complete serum-free culture medium, which was sufficient to bring the medium to the level of the scleral rim. The culture medium used was DMEM/F-12 containing 120 μg/mL Penicillin G, 200 μg/mL streptomycin sulfate and ITS premix. Samples were incubated at 37° C. in 5% $CO_2$ in the air with once daily medium changes.

Trypan blue solution was mixed into the SPAAC gel precursor solution to visualize the gel on the rabbit cornea. Alexa Fluor 647 was conjugated to the azide-PEG-collagen to visualize the collagen gels formed on the corneal wounds by fluorescence microscopy following manufacturer's protocol. Briefly, Alexa Fluor 647 reactive dye was mixed with azide-PEG-collagen and incubated for 2 hr at 4° C. and dialyzed via Slide-A-Lyzer dialysis kit overnight at 4° C. in PBS. SPAAC gels of 1.5 and 3.0 mg/mL with and without encapsulated keratocytes were applied to the cornea-scleral organ culture specimens after anterior lamellar keratectomy, and no treatment after lamellar keratectomy was used as a control. After 6 days, the corneas were fixed and stained with Phalloidin 488 and DAPI. The corneas were flat mounted and then analyzed by confocal microscopy for re-epithelization, keratocyte spreading, and presence of the gel.

Calculation of the molar ratio of collagen primary amine groups and the N-hydroxysuccinimide ester of azide-PEG-NHS and DBCO-sulfo-NHS. To evaluate the conjugation efficacy of click chemistry moieties, a fluorescamine assay was applied to quantify the number of primary amine groups present at lysine residues and protein's N-terminus. In our collagen conjugation step, NHS ester reacts with primary amines of collagen, which are reduced after conjugation. The decrease in primary amines can be measured by fluorescamine assay as a measure of conjugation conversion. The molar ratio NHS reagents and primary amine groups of collagen were determined (Table 1).

Each NHS reagent has one NHS group, and the number of primary amines of collagen was calculated based on the amino acid composition. Lotz et al. calculated the number of collagen primary amine groups, which was 111 (108 lysine residues and three N-terminus) per collagen molecule.

The molar equivalent volume of the azide-PEG-NHS solution (100 mg/mL in DMSO) was 3.5 μL for primary amines in 1 mL of neutralized collagen solution (3 mg/mL) and DBCO-sulfo-NHS solution (100 mg/mL in PBS) was 4.3 μL (see Table 1). Based on the calculation, the NHS reagents were applied to collagen with 0.25-5 molar ratios against primary amine groups, representing about 7.5-150 molar excess compared to collagen.

TABLE 1

NHS ester reagents for collagen conjugation.

| | Molecular weight [g/mol] | Solvent | Volume[a] of equivalent molar ratio[b] [μL] |
|---|---|---|---|
| Azide-PEG-NHS | 432.4 | DMSO | 3.5 |
| DBCO-sulfo-NHS | 532.5 | PBS | 4.3 |

[a]Volume of 100 mg/mL solution for 1 mL of 3 mg/mL neutralized collagen solution;
[b]Molar ratio between NHS ester and primary amine group in a collagen molecule.

EXAMPLES

The present invention is based on the discovery that bioorthogonal strain-promoted azide-alkyne cycloaddition (SPAAC) crosslinking is useful in producing in situ-forming (collagen) corneal stromal substitutes and constructs, such as crosslinked collagen gels, that may find application in-vivo in treating and reconstructing a surgically incised or wounded cornea in a mammalian subject, and in-vitro in studying keratocyte-keratinocyte interactions.

The following examples are put forth so as to provide those of ordinary skill in the art with a complete disclosure and description of how to make and use the present invention. The examples are offered for illustrative purposes only, and are not intended to limit the scope of what the inventors regard as their invention.

Reasonable efforts have been made to ensure accuracy with respect to numbers used, e.g. in the context of temperature, amount and such, but some experimental errors and deviations should be accounted for. Unless indicated otherwise, parts are parts by weight, molecular weight is average molecular weight, temperature is in degree Celsius, and pressure is at or near atmospheric. Standard abbreviations may be used throughout the specification, e.g. s or sec for second(s), min for minute(s), h or hr for hour(s), aa for amino acid(s), nt for nucleotide(s), kb for kilobase(s), i.v. for intravenous(ly), and the like.

Example 1

Generation of Crosslinked Collagen Hydrogels as In-Situ-Forming Corneal Constructs and their Mechanical Properties Collagen Conjugation For Gel Formation By SPAAC. Crosslinked collagen hydrogels were generated to assess their suitability as a matrix material for an in situ-forming corneal construct, as described herein. To facilitate strain-promoted azide-alkyne cycloaddition (SPAAC) mediated crosslinking, collagen was functionalized with either azide or dibenzocyclooctyne (DBCO) groups using N-hydroxysuccinimide (NHS) coupling chemistry.

A poly(ethylene glycol) (PEG) spacer was introduced in the azide group conjugation to allow for enhanced conjugation efficiency. The PEG spacer is hydrophilic, which can increase the stability of the conjugated group in aqueous solvents. The length of the PEG5 spacer, about 22 Å, was used to promote accessibility to the primary amines during conjugation, as well as to the cycloalkyne group during crosslinking by SPAAC. DBCO was chosen as the cyclooctyne group of the SPAAC reaction.

Conjugation efficiency. The conjugation efficiency was assessed using a fluorescamine based assay (FIG. 2). Fluorescamine is traditionally used to quantify protein content since it reacts rapidly with a protein's primary amine groups, which are found at lysine residues and the N-terminus, to create a fluorescent signal (FIG. 2, panel A). Since NHS reagents react with primary amine groups as well, the functionalization efficiency can be quantified by correlating fluorescence intensity to the number of the residual primary amine groups, where a reduced fluorescent signal indicates a higher degree of functionalization.

The fluorescence intensities were converted to concentration of primary amine groups using a standard curve of primary amine groups in collagen, and then the conversions were obtained by taking the ratio of the concentration of primary amine groups before and after conjugation (FIG. 2, panel B). The molar ratio between the collagen primary amine groups and the NHS groups of azide-PEG-NHS and DBCO-sulfo-NHS was calculated (Table 1). For equivalent molar ratio conjugation, the conversions of azide-PEG-collagen and DBCO-collagen were 55.87±4.57% and 59.50±3.93%, respectively. Increasing the molar ratio increased the conjugation efficiency, where the conversion of azide-PEG-collagen was 74.80±2.52% with the 2-fold molar ratio, and the conversion with 5-fold molar ratio was slightly increased, but there was no statistical difference between the two. The conversion of DBCO-collagen was 68.91±6.93% with the 2-fold molar ratio, and the conversion with 5-fold molar ratio was decreased without statistical difference. For both conjugation of azide-PEG and DBCO, the 2-fold molar ratio was the most effective condition for the reaction between primary amine and NHS groups.

Mechanical Properties Of Crosslinked Collagen Gels. The optical and mechanical properties of the SPAAC-crosslinked gels and non-crosslinked gels were analyzed to determine if the crosslinked collagen gels were suitable for use in the cornea. The SPAAC-crosslinked gel was observed to be relatively transparent while the non-crosslinked gel was relatively opaque (FIG. 3, panel A). To quantify this change in optical transparency, gel transmittance was evaluated at wavelengths between 350 and 800 nm. The transmittance of SPAAC-crosslinked gels remained constant at ~80% in the visible light range, while the transmittance of non-crosslinked collagen increased with wavelength from ~20 to 80% (FIG. 3, panel B). The average transmittance of SPAAC and non-crosslinked gels were 84.58±1.44% and 57.56±13.48%, respectively.

The mechanical properties of the collagen gels during and after gelation were measured using rheological methods (FIGS. 3, panels C and D). The storage modulus of the SPAAC crosslinked gel increased from ~10 to ~100 Pa over the 15 min time course, and the rate of the change in modulus steadily decreased overall time (FIG. 3, panel C). The non-covalently crosslinked gel's storage modulus fluctuated for ~450 s, and then steadily increased to reach ~40 Pa at 900 s (FIG. 3, panel C). After 900 s, the storage moduli of SPAAC and non-crosslinked gel were measured as a function of frequency from 0.1 to 10 Hz. e(FIG. 3, panel D). SPAAC-crosslinked gels showed linear viscoelastic responses as an elastic material in the range between 0.1-10 Hz, and non-covalently crosslinked collagen gels also showed overall similar response although there were unstable changes in the loss modulus in the range between 0.1-1 Hz.

Ratios Between Azide-PEG-Collagen And DBCO-Collagen. To assess if the mechanical properties could be modulated by crosslinking density, either the ratio between azide-PEG-collagen and DBCO-collagen or the collagen concentration was changed. First, the ratio of azide:DBCO was varied between 1:1 (100:100) and 3:1 (150:50) at a set collagen concentration of 3 mg/mL following complete gelation at room temperature. The storage moduli were measured and then converted to elastic moduli. In these cases, gels were treated as incompressible solids, to give a Poisson's ratio of 0.5, thus $E=3*G'$. The 1:1 (100:100) ratio of azide-PEG-collagen and DBCO-collagen showed the highest storage modulus, and the storage moduli decreased as the ratio shifted in either direction (FIG. 4, panel A).

The maximum storage modulus of the crosslinked collagen gel (1:1 or 100:100 ratio) was 84.83±9.30 Pa (FIG. 4, panel B), and the minimum was 25.99±4.08 Pa when the ratio of azide-PEG-collagen and DBCO-collagen was 3:1 (150:50), demonstrating that the crosslinking density can be used to tune the mechanical properties of the gels depending on the desired application of the material.

In addition, the concentration of functionalized collagen can also be used to change the gel mechanical properties and fabricate SPAAC gels with desired storage moduli (FIGS. 4, panels C and D). The storage modulus increased linearly with increasing collagen concentration, from 3.26±0.59 Pa to 81.05±10.72 Pa.

Example 2

Sustained Viability of Keratocytes and Keratinocytes on Crosslinked Collagen Gels Keratocytes And Keratinocytes Culture Using Crosslinked Collagen Gels. The sustained viability of keratocytes and keratinocytes encapsulated in and seeded on non-covalently crosslinked and chemically crosslinked collagen gels was assessed using Live/Dead staining to ensure that the gels are cytocompatible (FIG. 5, panel A). Viability remained greater than 70% after six days in culture in all cases, and there were no significant differences in cell viability between the non-crosslinked gel and SPAAC gels.

The morphology of encapsulated keratocytes was evaluated based on F-actin staining (FIG. 5, panel B). In 1.5 mg/mL SPAAC-crosslinked gels, encapsulated keratocytes showed dendritic morphologies at day 2, started to exhibit bipolar morphologies at day 4, and formed a cell network by day 6. In addition, keratocyte cell bodies were significantly larger in 1.5 mg/mL SPAAC-crosslinked gels compared to 3.0 mg/mL SPAAC-crosslinked gels and non-covalently crosslinked collagen gels.

Keratocytes encapsulated in the 3.0 mg/mL SPAAC-crosslinked gel exhibited a mostly round morphology, but some exhibited dendritic extensions at day 4. The keratocytes in physically crosslinked collagen gel exhibited dendritic morphologies with intensive branching at all time points. Additionally, the keratocyte cell bodies size increased significantly at day 4 compared to day 2. Encapsulated keratocytes produced keratan sulfate (KS), a matrix glycosaminoglycan, in crosslinked and non-crosslinked collagen gels and KS staining was observed in the cell cytoplasm (FIG. 5, panel C).

Keratinocytes were able to adhere and spread on top of the SPAAC-crosslinked gels based on F-actin staining, and ZO-1 and CK3 were expressed regardless of the type of gel (FIG. 5, panel D). Interestingly, keratinocytes seeded on SPAAC-crosslinked gels formed a confluent layer after 6 days in culture, but the same was not observed for the non-covalently crosslinked gel. Accordingly, the keratinocytes covered over 95% surface of SPAAC-crosslinked gels, and the cell coverage areas were significantly higher for SPAAC-crosslinked gels compared to non-crosslinked gels (FIG. 5, panel E).

Figure 6:
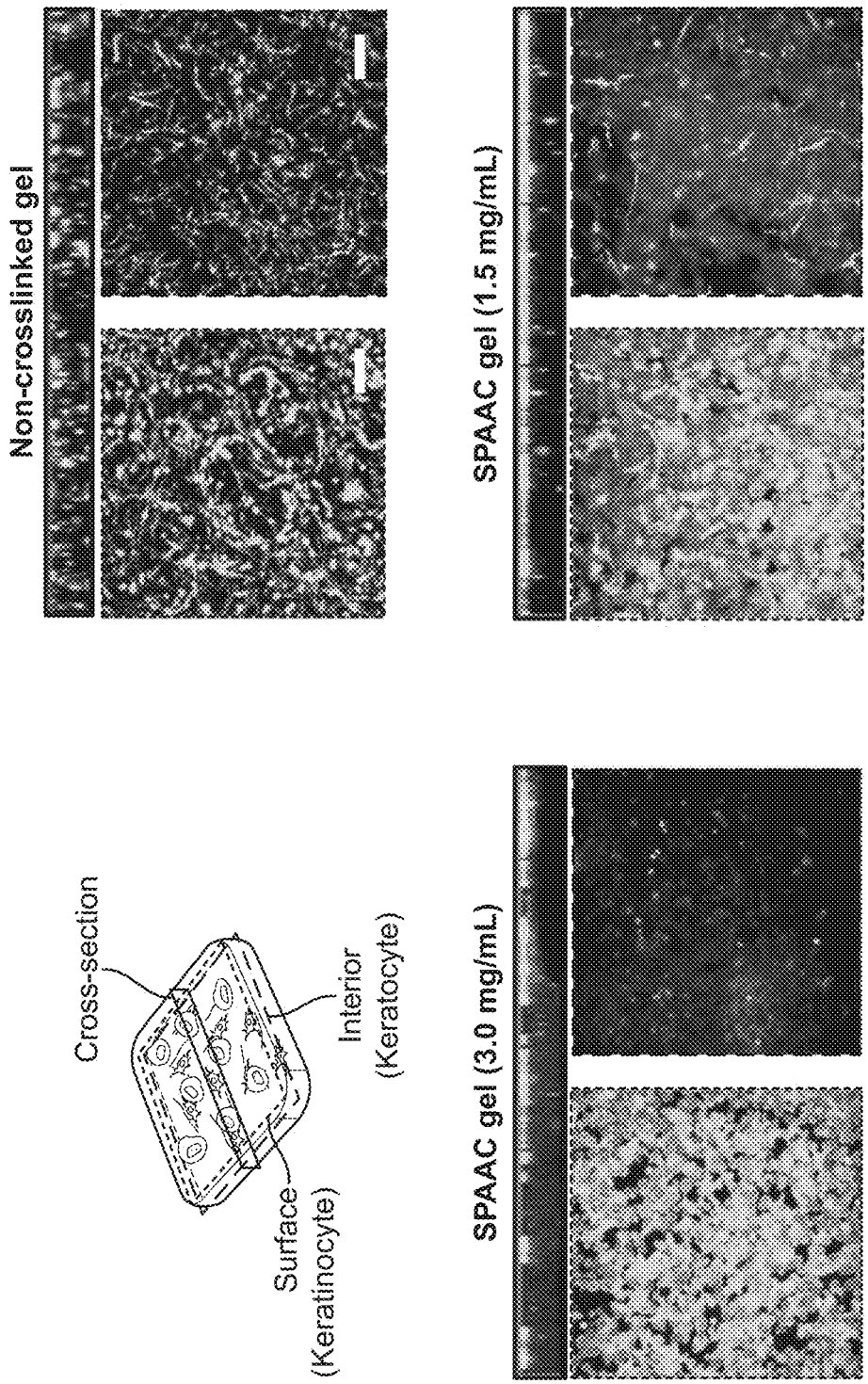
FIG. 6 shows a co-culture of human keratinocytes on the surface of and keratocytes encapsulated within SPAAC-crosslinked and non-covalently crosslinked collagen gels, respectively. The black frames are cross-sectional views that show keratinocytes on the surface of the scaffold and the keratocytes within the gels. The red and orange frames are surface and interior sections, respectively. F-actin (green) and nucleus (blue) were stained for both keratocytes and keratinocytes. The depth of cross-sectional images is 200 µm. Scale bars: 200 µm.
Figure 7A:
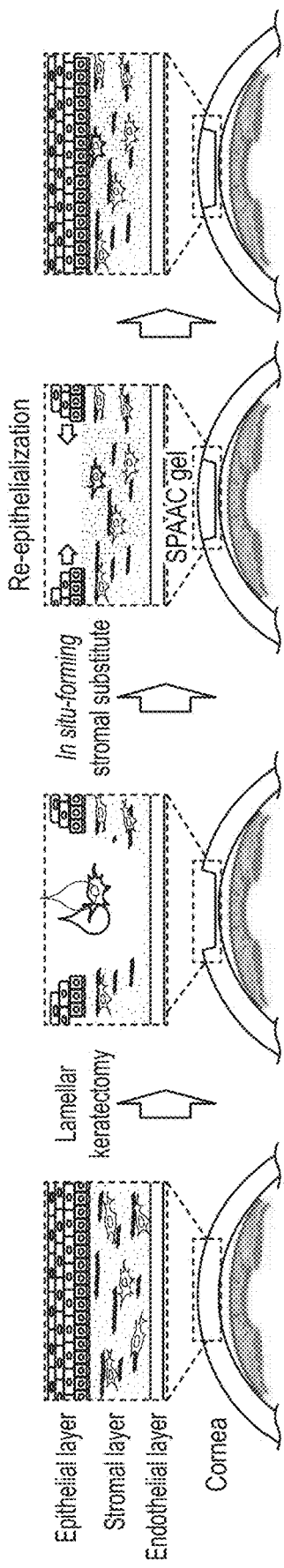
FIGS. 7A-7C illustrates the performance of SPAAC-crosslinked gel ("SPAAC gel") used as a substitute for corneal stromal tissue. (Panel FIG. 7A) Schematic of lamellar keratectomy and SPAAC gel treatment with keratocyte as an in situ-forming corneal stromal substitute, for either the filling-in and stabilization of deep corneal ulcers and/or the in a sutureless, in situ-forming lamellar keratoplasty ("SILK") procedure, where damaged or disease corneal tissue is removed and replaced with the injectable SPAAC gel precursor solution which is then crosslinked in situ at the corneal wound site. The gel conforms to the contours of the corneal wound it is filling, recreating the smooth surface contour and providing a suitable matrix for epithelialization (Panel FIG. B) Photographic images of rabbit corneal tissue with lamellar keratectomy and SPAAC gel application. (Panel FIG. C) Schematic and fluorescence images of no treatment and SPAAC-crosslinked gels with and without encapsulated keratocytes injected onto corneal tissue after lamellar keratectomy. F-actin (green) of cells was stained, and Alexa Fluor 647 (red) was conjugated to SPAAC-crosslinked gels. The white arrow represents fibroblastic transformation of resident keratocytes. Scale bars: 200 µm.
Figure 7A:
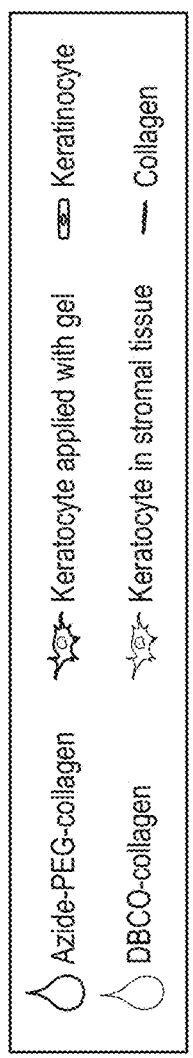
Figure 7B:
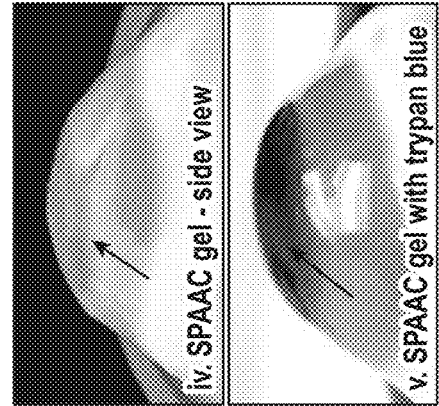
Figure 7B:
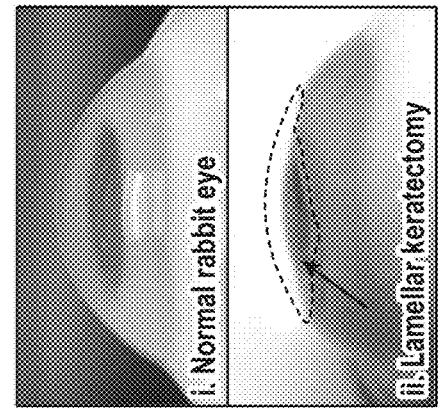
Figure 7C:
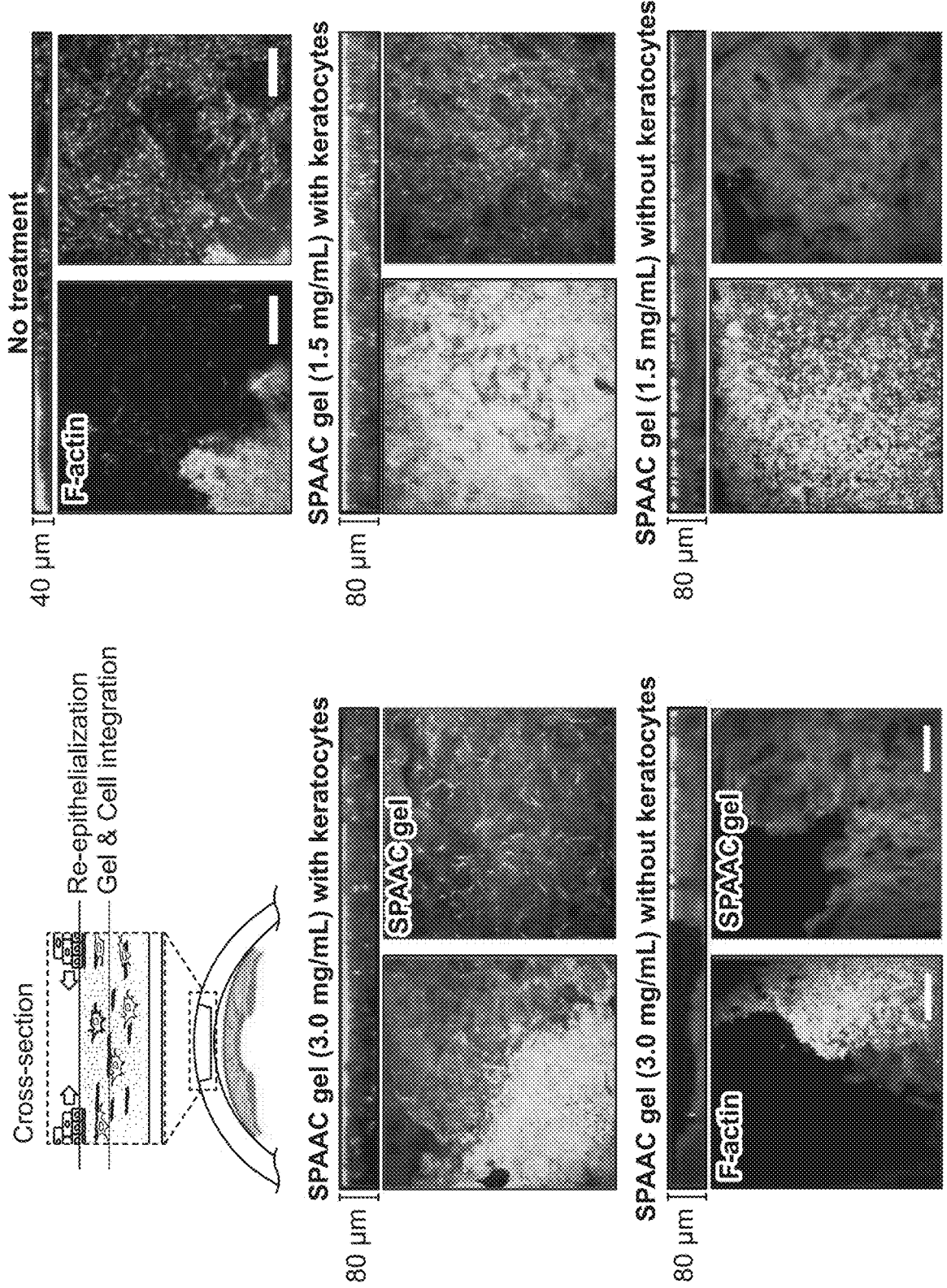

Lamellar Corneal Construct With Encapsulated Keratocytes And Seeded Keratinocytes. A lamellar corneal construct with epithelial and stromal layers was created through the encapsulation of keratocytes in SPAAC-crosslinked gels followed by the seeding of keratinocytes on top of SPAAC-crosslinked gel scaffolds. FIG. 6 shows both keratinocytes on gel surfaces and keratocytes within collagen gels.

The surface section represents the epithelial layer, formed by keratinocytes that grew to confluence over both concentrations of SPAACs-crosslinked gels. The deeper layers of the gels contained keratocytes, representing a cellularized stromal layer.

As illustrated in FIG. 5, panel B, keratocytes showed increased spreading in non-crosslinked and 1.5 mg/mL SPAAC-crosslinked gels, but the cells maintained rounded morphologies and showed reduced F-actin staining in 3.0 mg/mL SPAAC-crosslinked gel. Keratinocytes were able to adhere and spread in the presence of the keratocyte-encapsulated collagen gels. Keratinocytes formed a confluent layer for SPAAC-crosslinked gels but not for non-covalently crosslinked gels. For the non-covalently crosslinked gels, both keratinocytes and keratocytes were observed at the surface of the gel.

Example 3

Organ Culture Model of Sutureless In Situ-Forming Lamellar Keratoplasty

An embodiment of the SPAAC-crosslinked in situ-forming corneal stromal substitute was applied to an ex-vivo rabbit cornea organ culture model after keratectomy to evaluate the capacity of SPAAC-crosslinked gels to support a multi-layered epithelium. By achieving close-to-native re-epithelialization, such crosslinked compositions may be useful for treating (repairing) or reconstructing a surgically incised or wounded cornea in a mammalian subject.

A deep anterior lamellar keratoplasty was performed on ex vivo rabbit corneas, and the wound area was filled with SPAAC-crosslinked gels of two concentrations (3.0 mg/mL and 1.5 mg/mL) with and without encapsulated keratocytes prior to placement in organ culture (FIG. 7). FIG. 7, panel A, shows a corneal tissue schematic of a lamellar keratectomy, and the regeneration process that can occur with the application of a corneal substitute. The SPAAC-crosslinked gel comprising encapsulated keratocytes filled the cavity produced by lamellar keratectomy or corneal damage, and provides a matrix structure for re-epithelialization.

A lamellar keratectomy was performed on rabbit cornea tissue, and a 1:1 mixture of azide-PEG-collagen and DBCO-collagen was applied to the wound site to form a gel (FIG. 7, panel B). The SPAAC-crosslinked gel (SPAAC gel) on the rabbit corneal surface was transparent and difficult to visually distinguish from native corneal tissue. Trypan blue solution was mixed in to better visualize the gel, which helped to reveal that the gel retained a smooth surface once placed into the wound.

The native rabbit corneal cells were visualized with F-actin staining after they had been treated with the SPAAC-crosslinked gel following lamellar keratectomy in comparison to untreated controls (FIG. 7, panel C). In untreated controls, where the stromal substitute had not been applied after the lamellar keratectomy, little migration of keratinocytes was observed in the epithelial layer, and the defect was not fully covered in the observed timeframe. Also, the number of remaining resident keratocytes with myofibroblastic transformation was increased in untreated controls.

In treated rabbit corneas, to which 3.0 mg/mL concentration SPAAC-crosslinked gel was added as a stromal substitute along with keratocytes, the keratocytes were able to encapsulate, i.e. spread within the gels, and the keratinocytes migrated on the surface of the gel. Although the keratinocytes did not cover the entire surface, they migrated onto the stromal substitute with higher density and more organized structures than on untreated controls.

In treated rabbit corneas, to which 1.5 mg/mL concentration SPAAC-crosslinked gel was added, the migration of keratinocytes and the spreading of encapsulated keratocytes was observed as well. The re-epithelialization by keratinocytes was vigorous as indicated by a high cell density and well-organized structure.

To investigate whether the host keratocytes migrate into the applied stromal substitute, the SPAAC-crosslinked gel was applied without the addition of keratocytes and keratinocytes (acellular gel). While epithelial cell migration over the collagen gel matrix was observed in the SPAAC-crosslinked, but acellular gel, keratocytes were not observed in the SPAAC-crosslinked, acellular gels for both 1.5 and 3.0 mg/mL concentrations (FIG. 7, panel C).

Figure 8:
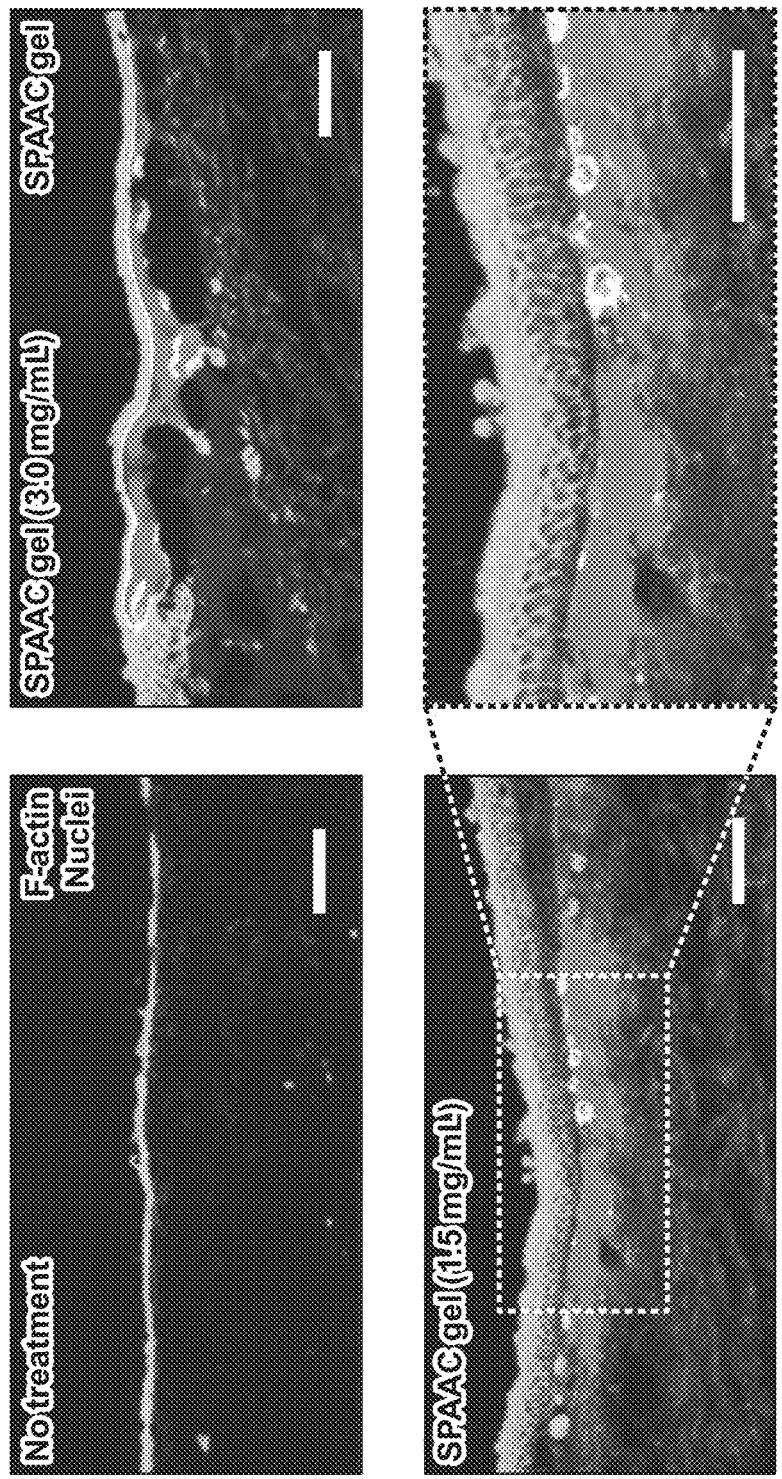
FIG. 8 shows fluorescence images of corneal tissue sections. F-actin (green) and nuclei (blue) of cells was stained, and Alexa Fluor 647 (red) was conjugated to SPAAC gels. Scale bars: 100 µm.
Figure 9:
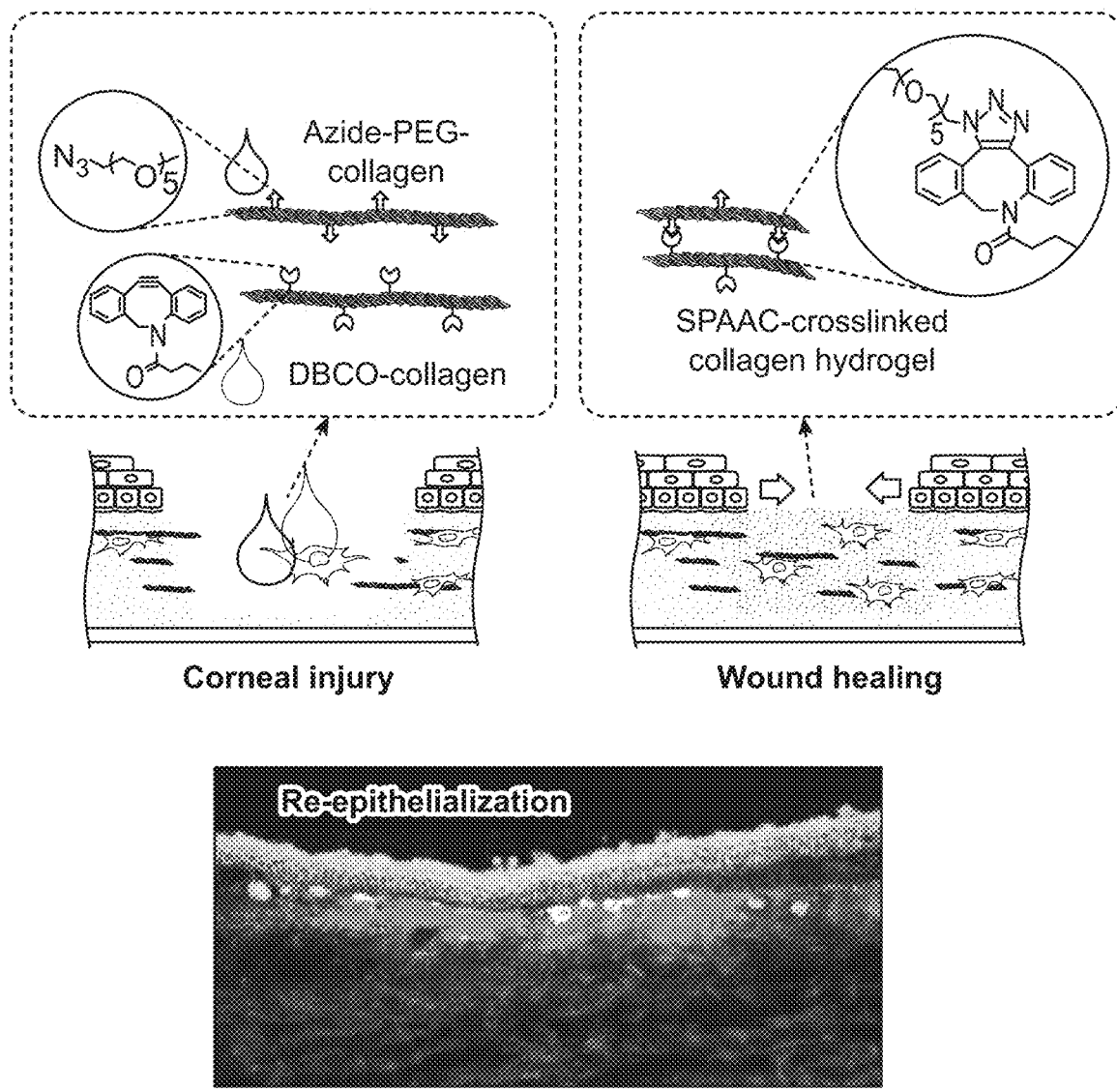
FIG. 9 is an illustration of the proposed reepithelization of a corneal wound using a bio-orthogonally crosslinked, in situ-formed collagen hydrogel.
Figures 10A, 10B:
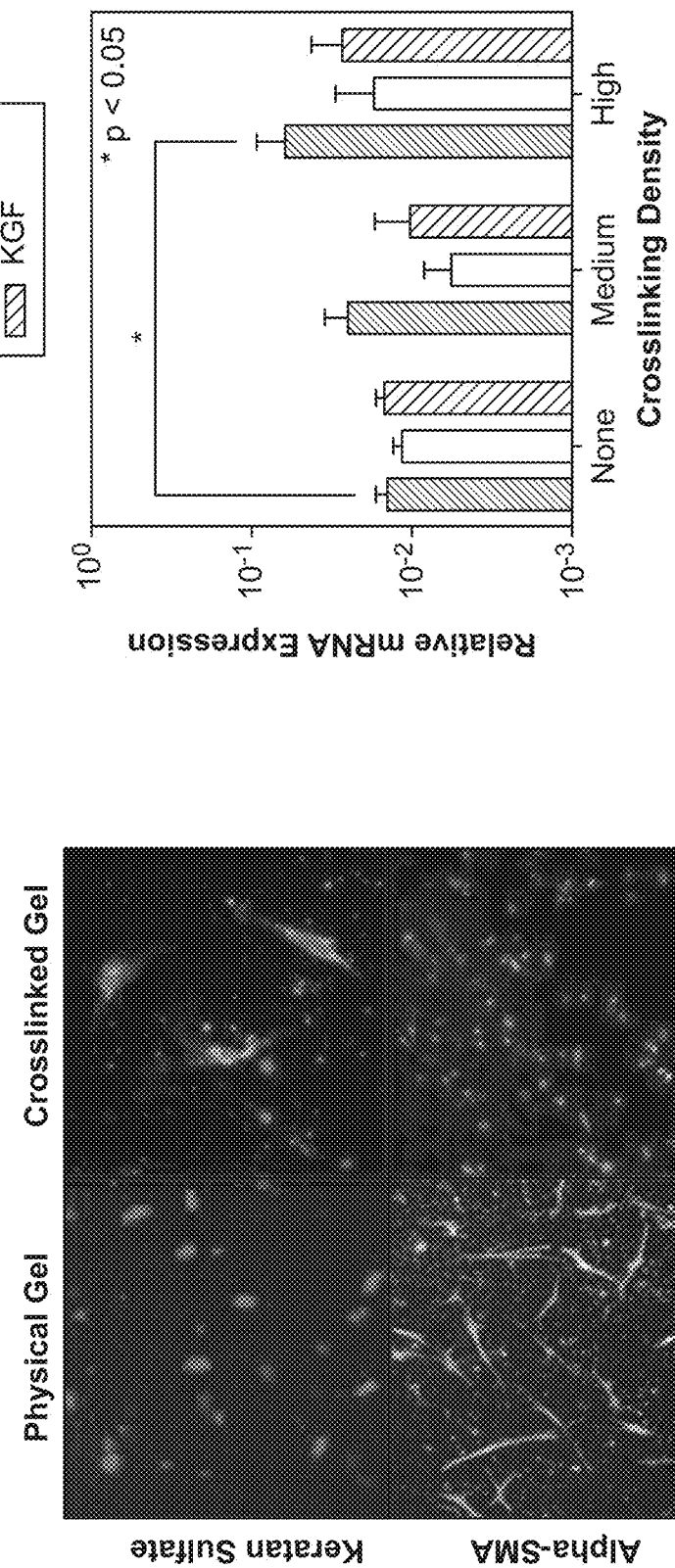
FIG. 10A-10B.
Figure 11:
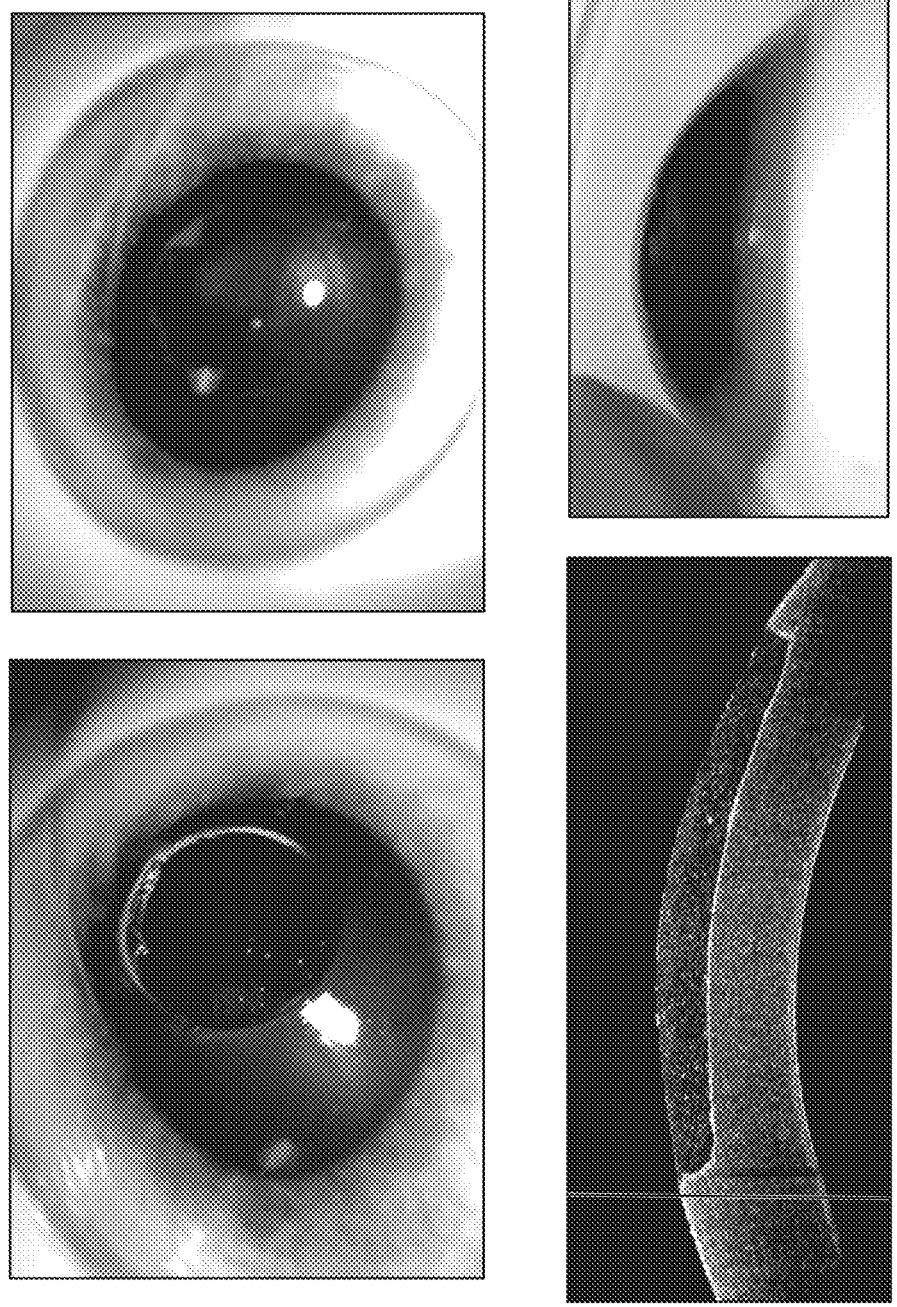
FIG. 11. Photographs (left to right) of a normal porcine eye following lamellar keratectomy, keratectomized porcine eye after application of an in situ forming gel, and OCT image of the porcine cornea with gel formed within stromal cavity. Side view showing the re-creation of a smooth, curved surface on the cornea after applying the gel to the deep stromal wound. The gel precursor solutions were applied and mixed directly on the wound and allowed to crosslink in situ.

Epithelial Layering In Keratocytes and Keratinocytes-Containing SPAAC-Crosslinked Gels. The tissues were sectioned, and the cross-section of corneal tissues was observed after staining of F-actin and nuclei (FIG. 8). Immunohistological processing of the corneal tissue without gel treatment after keratectomy showed epithelial layer formation on the wound site, but the layer remained a monolayer.

The application of 3.0 mg/mL concentration SPAAC-crosslinked gel allowed a multi-layered epithelial layer (2-3 layers) over the gel surface. The interface between the gel and epithelial layer was uniform and well assembled, while there were vacant spaces between the gel and stromal layer in some areas.

The 1.5 mg/mL concentration SPAAC-crosslinked gel treatment supported the growth of a multi-layered epithelium, 4-5 layers thick with near-normal appearing stratified morphology. The 1.5 mg/mL SPAAC-crosslinked gel also showed good apposition with both the overlying epithelial and underlying stromal layers.

In conclusion, by achieving close-to-native re-epithelialization, embodiments of the crosslinked, in situ-forming corneal stromal substitute are promising candidates for lamellar and defect reconstruction of corneal stromal tissue. Furthermore, most likely as a result of their superior substrate stiffness, gel integrity, and resistance to degradation, the crosslinked corneal stromal substitutes support stable keratinocyte morphology on their surface. Therefore, their efficacy for re-epithelialization in the context of reconstructing a surgically incised or wounded cornea in a mammalian subject can be enhanced with the addition of keratocytes and keratinocytes.

Example 4

Generation of Crosslinked Collagen Hydrogels Using Multi-Arm PEG Crosslinkers

Poly(ethylene glycol) (PEG) Conjugation for Collagen Hydrogel Formation by SPAAC. Multi-arm PEG molecules were used to crosslink azide-functionalized collagen, as previously described, to form in-situ forming hydrogels. To facilitate SPAAC crosslinking, 2, 3, 4, or 8-arm PEG molecules were modified with bicyclo[6.1.0]nonyne (BCN) using N-hydroxysuccinimide (NHS) coupling chemistry. Some or all of the functional groups on the PEG may be modified.

Multi-arm PEG molecules are used here as a biologically inert polymer crosslinking species to crosslink the azide-containing collagen biopolymer. The multi-arm PEG may be functionalized with any alkyne that will participate in the SPAAC reaction. Increasing the number of functional groups (number of arms per PEG molecule) will increase the stiffness of the hydrogel network and initial gelation rate for a given PEG concentration due to the increased number of crosslinking sites.

The conjugation efficiency of the PEG conjugation can be assessed using a fluorescamine based assay, as described previously. Similar to the collagen conjugation, a reduced fluorescent signal from the PEG correlates to a higher conjugation efficiency.

The mechanical properties of collagen-PEG SPAAC crosslinked hydrogels. The mechanical properties of the collagen-PEG SPAAC crosslinked hydrogels can be changed solely by changing the PEG concentration and the functionality (number of arms) of the PEG crosslinking molecules. Changes in mechanical properties can be made independently of the collagen concentration. For example, holding the collagen and PEG molar concentrations constant, and changing the PEG functionality from 2-arm PEG to 8-arm PEG, 4 times more crosslinks are expected be formed, corresponding to an increase in stiffness. Alternatively, the collagen concentration and PEG functionality can be held constant and the PEG concentration reduced 5-fold. This will decrease the mechanical stiffness of the hydrogel without changing the collagen content. These collagen-PEG hydrogels should show similar crosslinking gelation behavior as the previously described all-collagen SPAAC crosslinked hydrogels. Similarly, their viscoelastic behavior will likely be unchanged over the frequencies commonly probed, from 0.1-1 Hz.

While the present invention has been described with reference to the specific embodiments thereof, it should be understood by those skilled in the art that various changes may be made, and equivalents may be substituted without departing from the true spirit and scope of the invention.

REFERENCES a) F. W. Price, M. T. Feng, M. O. Price, Cornea 2015, 34, S41; b) S. Matthyssen, B. Van den Bogerd, S. N. Dhubhghaill, C. Koppen, N. Zakaria, Acta Biomater. 2018, 69, 31.

Gain et al., JAMA Ophthalmology 2016, 134, 167.

Fagerholm et al. Sci. Transl. Med. 2010, 2, 46ra61; Fagerholm, et al. Clin. Transl. Sci. 2009, 2, 162; Fagerholm et al. Griffith, Biomaterials 2014, 35, 2420; Buznyk et al. Clin. Transl. Sci. 2015, 8, 558.

Sheehy et al. in Peptides and Proteins as Biomaterials for Tissue Regeneration and Repair, DOI: 10.1016/b978-0-08-100803-4.00005-x (Ed: M. C. L. Martins), Woodhead Publishing 2018, p. 127; b) X. Duan, H. Sheardown, Biomaterials 2006, 27, 4608; c) I. Rault, V. Frei, D. Herbage, N. Abdul-Malak, A. Huc, J. Mater. Sci. Mater. Med. 1996, 7, 215.

a) C. M. Madl, L. M. Katz, S. C. Heilshorn, Adv. Funct. Mater. 2016, 26, 3612; b) M. F. Debets, S. S. van Berkel, J. Dommerholt, A. J. Dirks, F. P. J. T. Rutjes, F. L. van Delft, Acc. Chem. Res. 2011, 44, 805; c) J. Zheng, L. A. Smith Callahan, J. Hao, K. Guo, C. Wesdemiotis, R. A. Weiss, M. L. Becker, ACS Macro Letters 2012, 1, 1071.

Udenfriend et al., Science 1972, 178, 871. Myung et al. Journal of Biomedical Materials Research Part A 2009, 90A, 70.

C. E. Willoughby, M. Batterbury, S. B. Kaye, Surv. Ophthalmol. 2002, 47, 174.

B. Kong, W. Sun, G. Chen, S. Tang, M. Li, Z. Shao, S. Mi, Sci. Rep. 2017, 7, 970.

R. M. Gouveia, C. J. Connon, in Biomaterials and Regenerative Medicine in Ophthalmology, DOI: 10.1016/b978-0-08-100147-9.00007-9, Woodhead Publishing 2016, p. 151.

G. Charriere, M. Bejot, L. Schnitzler, G. Ville, D. J. Hartmann, J. Am. Acad. Dermatol. 1989, 21, 1203.

B. R. Williams, R. A. Gelman, D. C. Poppke, K. A. Piez, J. Biol. Chem. 1978, 253, 6578.

H. J. Lee, G. M. Fernandes-Cunha, I. Putra, W.-G. Koh, D. Myung, ACS Appl. Mater. Interfaces 2017, 9, 23389.

G. T. Hermanson, in Bioconjugate Techniques, DOI: 10.1016/b978-0-12-382239-0.00018-2, Academic Press, Boston 2013, p. 787.

C. Lotz, F. F. Schmid, E. Oechsle, M. G. Monaghan, H. Walles, F. Groeber-Becker, ACS Appl. Mater. Interfaces 2017, 9, 20417.

S. M. Thomasy, V. K. Raghunathan, M. Winkler, C. M. Reilly, A. R. Sadeli, P. Russell, J. V. Jester, C. J. Murphy, Acta Biomater. 2014, 10, 785.

X. Ma, M. E. Schickel, Mark D. Stevenson, Alisha L. Sarang-Sieminski, Keith J. Gooch, Samir N. Ghadiali, Richard T. Hart, Biophys. J. 2013, 104, 1410.

H. E. Murrey, J. C. Judkins, C. W. am Ende, T. E. Ballard, Y. Fang, K. Riccardi, L. Di, E. R. Guilmette, J. W. Schwartz, J. M. Fox, D. S. Johnson, J. Am. Chem. Soc. 2015, 137, 11461.

J. W. Ruberti, J. D. Zieske, Prog. Retin. Eye Res. 2008, 27, 549.

a) W. Petroll, N. Lakshman, Journal of Functional Biomaterials 2015, 6, 222; b) N. Lakshman, A. Kim, W. M. Petroll, Exp. Eye Res. 2010, 90, 350.

J. Kanta, Cell Adhesion & Migration 2015, 9, 308.

N. Garagorri, S. Fermanian, R. Thibault, W. M. Ambrose, O. D. Schein, S. Chakravarti, J. Elisseeff, Acta Biomater. 2008, 4, 1139.

M. P. Beales, J. L. Funderburgh, J. V. Jester, J. R. Hassell, Invest. Ophthalmol. Vis. Sci. 1999, 40, 1658.

S. Mi, B. Chen, B. Wright, C. J. Connon, Journal of Biomedical Materials Research Part A 2010, 95A, 447.

M. E. Fini, Prog. Retin. Eye Res. 1999, 18, 529.

A. Sorkio, L. Koch, L. Koivusalo, A. Deiwick, S. Miettinen, B. Chichkov, H. Skottman, Biomaterials 2018, 171, 57.

a) M. Griffith, R. Osborne, R. Munger, X. Xiong, C. J. Doillon, N. L. C. Laycock, M. Hakim, Y. Song, M. A. Watsky, Science 1999, 286, 2169; b) M. Griffith, M. Hakim, S. Shimmura, M. A. Watsky, F. Li, D. Carlsson, C. J. Doillon, M. Nakamura, E. Suuronen, N. Shinozaki, K. Nakata, H. Sheardown, Cornea 2002, 21, S54.

S. Hayes, P. Lewis, M. M. Islam, J. Doutch, T. Sorensen, T. White, M. Griffith, K. M. Meek, Acta Biomater. 2015, 25, 121.

M. Griffith, M. A. Watsky, C.-Y. Liu, in Methods of Tissue Engineering (Eds: A. Atala, R. Lanza), Academic Press, N Y 2001, p. 131.

M. D. M. Evans, G. A. McFarland, R. Z. Xie, S. Taylor, J. S. Wilkie, H. Chaouk, Biomaterials 2002, 23, 1359.

C. Lotz, F. F. Schmid, E. Oechsle, M. G. Monaghan, H. Walles, F. Groeber-Becker, ACS Appl. Mater. Interfaces 2017, 9, 20417.

What is claimed is:

1. An in-situ-forming corneal construct composition comprising:
    a first composition comprising a polymer comprising collagen that is functionalized with dibenzocyclooctyne (DBCO) or bicyclooctyne, and
    a second composition comprising a polymer comprising collagen that is functionalized with azide linked through a polyethylene glycol spacer,
    wherein the collagen is present at a concentration of from 1.5 to 3 mg/ml, and the ratio of the first and second compositions are from 1:3 to 3:1,
    wherein the first and second compositions are mixed such that the first and second compositions reacts in a strain-promoted azide-alkyne cycloaddition (SPAAC) reaction to covalently link and form a defined gel structure in situ without the need for an external energy source, and
    wherein the construct composition comprises corneal stem cells, keratocytes, keratocyte precursors, keratinocytes, or keratinocyte precursors encapsulated within said formed gel.

2. The construct composition of claim 1, wherein keratocytes are encapsulated within the gel.

3. A method of treating or reconstructing a surgically incised or wounded corneal area in a mammalian subject in need thereof, comprising:
    mixing a first composition comprising collagen functionalized with dibenzocyclooctyne (DBCO) or bicyclooctyne, and a second composition comprising a polymer comprising collagen functionalized with azide to create a mixture, and
    applying the mixture to the wounded corneal area;
    wherein collagen is present at a concentration of from 1.5 to 3 mg/ml in the mixture;
    wherein the ratio of the first and second compositions are from 1:3 to 3:1;
    wherein the azide is linked to collagen through a polyethylene glycol spacer;
    wherein the mixture comprises cells selected from the group consisting of corneal stem cells, keratocytes, keratocyte precursors, keratinocytes, and keratinocyte precursors; and
    wherein the first and second compositions react in a strain-promoted azide-alkyne cycloaddition (SPAAC) reaction to covalently link and form a defined gel structure on the wounded corneal area in situ without the need for an external energy source.

4. The method of claim 3, wherein the mixture comprises keratocytes.

* * * * *

UNITED STATES PATENT AND TRADEMARK OFFICE
CERTIFICATE OF CORRECTION

| | |
|---|---|
| PATENT NO. | : 12,036,314 B2 |
| APPLICATION NO. | : 17/251605 |
| DATED | : July 16, 2024 |
| INVENTOR(S) | : David Myung et al. |

It is certified that error appears in the above-identified patent and that said Letters Patent is hereby corrected as shown below:

In the Specification

Column 1, Lines 14-16, should read as follows:
"This invention was made with Government support under contract 1542152 awarded by the National Science Foundation and under contract EY028176 awarded by the National Institutes of Health. The Government has certain rights in the invention."

Signed and Sealed this
Tenth Day of September, 2024

Katherine Kelly Vidal
*Director of the United States Patent and Trademark Office*